(12) United States Patent
Maddaford et al.

(10) Patent No.: US 6,251,893 B1
(45) Date of Patent: Jun. 26, 2001

(54) BICYCLIC PIPERIDINE AND PIPERAZINE COMPOUNDS HAVING 5-HT$_6$ RECEPTOR AFFINITY

(75) Inventors: Shawn Maddaford, Mississauga; Tao Xin, North York; Abdelmalik Slassi; Ashok Tehim, both of Mississauga, all of (CA); Qi Qiao, Nutley, NJ (US)

(73) Assignee: NPS Allelix Corp., Ontario (CA)

( * ) Notice: Subject to any disclaimer, the term of this patent is extended or adjusted under 35 U.S.C. 154(b) by 0 days.

(21) Appl. No.: 09/156,495

(22) Filed: Sep. 18, 1998

Related U.S. Application Data

(63) Continuation-in-part of application No. 09/097,008, filed on Jun. 13, 1998.

(51) Int. Cl.[7] ............... A61K 31/55; A61K 31/44; A61P 25/18; C07D 221/02; C07D 241/36
(52) U.S. Cl. ............... 514/214.01; 514/214.02; 514/249; 514/299; 514/306; 540/579; 540/593; 544/349; 546/112; 546/138; 546/183
(58) Field of Search ............... 540/579, 593; 544/349; 546/112, 138, 183; 514/214.01, 249, 299, 306

(56) References Cited

U.S. PATENT DOCUMENTS 5,874,427 * 2/1999 Filla et al. .................. 514/214

OTHER PUBLICATIONS

International Publication No. WO97/28162 published Aug. 7, 1997.
International Publication No. WO97/11949 published Apr. 3, 1997.
Rehse, K., et al., Arch. Pharm. 1994, 327,67–75.
Repke, D.B., et al., J. Org. Chem. 1994, 59, 2164–2171.
Rehse, K., et al.; Arch. Pharm. 1987, 320, 1072–1083.
King, F. D., J. Chem. Soc. Perkin trans. I, 1986, 447–453.
Royer, J., et al., Nouveau Journal de Chimie, 1981, 5, 581–585.
Freter, K., J. Org. Chem., 1975, 40, 2525–2529.

\* cited by examiner

*Primary Examiner*—Mukund J. Shah
*Assistant Examiner*—Brenda Coleman
(74) *Attorney, Agent, or Firm*—Arent Fox Kintner Plotkin Kahn

(57) ABSTRACT

Described herein are compounds with affinity for the 5-HT$_6$ receptor, which have the general formula:

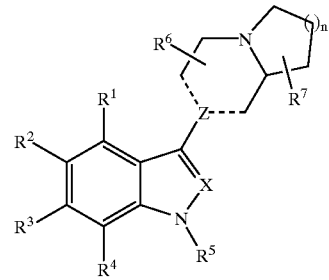

I wherein $R^1$, $R^2$, $R^3$ and $R^4$ are independently selected from the group consisting of H, halo, OH, $C_{1-6}$alkyl, $C_{1-6}$alkoxy, $C_{2-6}$alkenyl, $C_{2-6}$alkynyl, $C_{3-7}$cycloalkyl and others;

$R^5$ is selected from the group consisting of $SO_2Ar$, $C(O)Ar$, Ar and $CH_2Ar$;

$R^6$ and $R^7$ are independently selected from the group consisting of H, $C_{1-6}$alkyl, optionally substituted phenyl and optionally substituted benzyl;

——— represents a single or double bond;

n is selected from an integer of from 1–3;

X is selected from the group consisting of $CR^{17}$ and N;

Z is selected from the group consisting of C, CH and N, provided that when ——— is a double bond, Z is C and when ——— is a single bond, Z is selected from CH and N;

Ar is an optionally substituted aromatic group selected from the group consisting of phenyl, pyridyl, thienyl, furanyl, naphthyl, quinolyl and isoquinolyl;

$R^{16}$ is selected from the group consisting of H, $C_{1-6}$alkyl and benzyl.

Also described is the use of these compounds as pharmaceuticals to treat indications where inhibition of the 5-HT$_6$ receptor is implicated, such as schizophrenia.

30 Claims, No Drawings

BICYCLIC PIPERIDINE AND PIPERAZINE COMPOUNDS HAVING 5-HT$_6$ RECEPTOR AFFINITY

This application is a continuation-in-part of U.S. Ser. No. 09/097,008, filed Jun. 13, 1998.

This invention relates to indole compounds having affinity for the serotonin 5-HT$_6$ receptor, to pharmaceutical and diagnostic compositions containing them and to their medical use, particularly in the diagnosis and treatment of CNS conditions.

According to one aspect of the invention, there are provided compounds of Formula I and a salt, solvate of hydrate thereof:

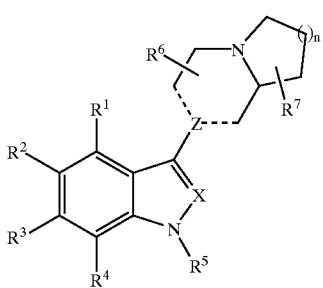

I wherein:
$R^1, R^2, R^3$ and $R^4$ are independently selected from the group consisting of H, halo, OH, $C_{1-6}$alkyl, $C_{1-6}$alkoxy, $C_{2-6}$alkenyl, $C_{2-6}$alkynyl, $C_{3-7}$cycloalkyl, $C_{4-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $NR^8R^9$, $C(O)NR^8R^9$, $SO_2NR^8R^9$, $CH_2SO_2NR^8R^9$, $CO_2R^{10}$, NHC(O)$R^{11}$, NHC(NR$^{12}$)$R^{11}$, C(NR$^{13}$)NR$^{14}R^{15}$, C(O)$R^{16}$, OC(O)$R^{16}$, SCF$_3$, SO$_2$CF$_3$, formyl, CF$_3$ and CF$_3$O;

$R^5$ is selected from the group consisting of SO$_2$Ar, C(O)Ar, CH$_2$Ar and Ar;

$R^6$ is independently selected from the group consisting of H, $C_{1-6}$alkyl, optionally substituted phenyl and optionally substituted benzyl $R^7$ is independently selected from the group consisting of H, $C_{1-6}$alkyl, $C_{1-6}$alkoxy, $C_{1-6}$alkylthio, optionally substituted phenyl, optionally substituted benzyl, optionally substituted phenoxy and optionally substituted benzyloxy;

——— represents a single or double bond, provided that there is only one double bond in the ring at a time;

n is selected from an integer of from 1–3;

X is selected from the group consisting of CR$^{17}$ and N;

Z is selected from the group consisting of C, CH and N, provided that when ——— is a double bond, Z is C and when ——— is a single bond, Z is selected from CH and N;

Ar is an optionally substituted aromatic group selected from the group consisting of phenyl, pyridyl, thienyl, furanyl, naphthyl, quinolyl and isoquinolyl wherein the optional substituents are independently selected from 1–4 members of the group consisting of halo, OH, $C_{1-6}$alkyl, $C_{1-6}$alkoxy, $C_{1-6}$alkylthio, CF$_3$ and CF$_3$O;

$R^8$, $R^9$ and $R^{10}$ are independently selected from the group consisting of H, $C_{1-6}$alkyl and phenyl or $R^8$ and $R^9$ may form an alkylene chain, —(CH$_2$)$_m$—, where m=3–6, to form, together with the nitrogen to which they are attached a 4- to 7- membered ring;

$R^{11}$ is selected from the group consisting of $C_{1-6}$alkyl, $C_{1-6}$alkoxy, phenyl, phenoxy, NH$_2$, alkylamino, dialkylamino, benzyl and benzyloxy;

$R^{12}$ is selected from the group consisting of H and $C_{1-6}$alkyl;

$R^{13}$ is selected from the group consisting of H and $C_{1-6}$alkyl;

$R^{14}$ and $R^{15}$ are independently selected from the group consisting of H and $C_{1-6}$alkyl or one of $R^{14}$ and $R^{15}$, together with $R^3$, forms an alkylene chain, —(CH$_2$)$_p$—, where p=2 or 3, bridging the nitrogen atoms to which they are attached;

$R^{16}$ is selected from the group consisting of optionally substituted phenyl, optionally substituted pyridyl, optionally substituted thienyl, optionally substituted furanyl and optionally substituted naphthyl; and $R^{17}$ is selected from the group consisting of H, $C_{1-6}$alkyl and benzyl.

It is an aspect of the invention to provide compounds which bind to the 5-HT$_6$ receptor.

According to another aspect of the invention, there is provided a pharmaceutical composition comprising a compound of Formula I in an amount effective to antagonize the 5-HT$_6$ receptor, and a pharmaceutically acceptable carrier.

In another aspect of the invention there are provided compositions containing a compound of Formula I in amounts for pharmaceutical use to treat CNS conditions where a 5-HT$_6$ antagonist is indicated, for example, for the treatment or prevention of central nervous system disturbances such as psychosis, schizophrenia, manic depression, depression, neurological disturbances, memory disturbances, Parkinsonism, amylotrophic lateral sclerosis, Alzheimer's disease and Huntington's disease.

In another aspect of the invention, there are provided compounds useful as intermediates in the preparation of compound of Formula I and having a general structure according to Formula II:

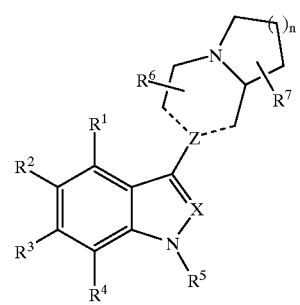

II wherein:
$R^5$ is H and $R^1$–$R^4$, $R^6$–$R^{17}$, X, Z, n and ——— are as defined in Formula I and a salt, solvate or hydrate thereof.

These and other aspects of the present invention are described in greater detail hereinbelow.

DETAILED DESCRIPTION AND PREFERRED EMBODIMENTS

The term "$C_{1-6}$alkyl" as used herein means straight and branched chain alkyl radicals containing from one to six carbon atoms and includes methyl, ethyl, propyl, isopropyl, t-butyl and the like.

The term "$C_{1-6}$alkoxy" as used herein means straight and branched chain alkoxy radicals containing from one to six carbon atoms and includes methoxy, ethoxy, propyloxy, isopropyloxy, t-butoxy and the like.

The term "$C_{2-4}$alkenyl" as used herein means straight and branched chain alkenyl radicals containing from two to six carbon atoms and includes ethenyl, 1-propenyl, 1-butenyl and the like.

The term "$C_{2-6}$alkynyl" as used herein means straight and branched chain alkynyl radicals containing from two to six carbon atoms and includes 1-propynyl (propargyl), 1-butynyl and the like.

The term "$C_{3-7}$cycloalkyl" as used herein means saturated carbocyclic radicals containing from 3–7 carbon atoms and includes cyclopropyl, cyclohexyl and the like.

The term "$C_{3-7}$cycloalkyloxy" as used herein means saturated carbocyclo-oxy radicals containing from 3–7 carbon atoms and includes cyclopropyloxy, cyclohexyloxy and the like.

The term "$C_{3-7}$cycloalkylthio" as used herein means saturated carbocycloalkylthio radicals containing from 3–7 carbon atoms and includes cyclopropylthio, cyclohexylthio and the like.

The term "$C_{2-7}$alkanoyl" as used herein means straight and branched chain alkanoyl radicals (—C(O)$C_{1-6}$alkyl) containing from 2–7 atoms and includes acetyl, propionyl, butyryl and the like.

The term "$C_{2-7}$alkanoyloxy" as used herein means straight and branched chain alkanoyloxy radicals (—OC(O) $C_{1-6}$alkyl) containing from 2–7 carbon atoms and includes acetoxy, propionyloxy, butyryloxy and the like.

The term "$C_{4-7}$cycloalkenyl" as used herein means carbocyclic radicals containing from 4–7 carbon atoms and 1 unit of unsaturation and includes cyclopent-1-enyl, cyclohex-1-enyl and the like.

The term "optionally substituted phenyl" as used herein means an unsubstituted phenyl radical or a phenyl radical substituted with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted pyridyl" as used herein means an unsubstituted pyridyl radical or a pyridyl radical substituted with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted naphthyl" as used herein means an unsubstituted naphthyl radical or a naphthyl radical substituted with 1–4 substituents independently selected from halo, OH, $C_{1-6}$alkyl, $C_{1-6}$alkoxy, $C_{1-6}$alkylthio, $CF_3$ and $CF_3O$.

The term "optionally substituted phenoxy" as used herein means an unsubstituted phenoxy radical or a phenoxy radical substituted with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted thienyl" as used herein means an unsubstituted thienyl radical or a thienyl radical substituted with 1–2 substituents independently selected from halo, OH, $C_{1-6}$alkyl, $C_{1-6}$alkoxy, $C_{1-6}$alkylthio, $CF_3$ and $CF_3O$.

The term "optionally substituted furanyl" as used herein means an unsubstituted furanyl radical or a furanyl radical substituted with 1–2 substituents independently selected from halo, OH, $C_{1-6}$alkyl, $C_{1-6}$alkoxy, $C_{1-6}$alkylthio, $CF_3$ and $CF_3O$.

The term "optionally substituted benzyl" as used herein means an unsubstituted benzyl radical or a benzyl radical substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "optionally substituted benzyloxy" as used herein means an unsubstituted benzyloxy radical or a benzyloxy radical substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "alkylamino" as used herein means an amino radical which is monosubstituted with a $C_{1-6}$alkyl group.

The term "dialkylamino" as used herein means an amino radical which is disubstituted with $C_{1-6}$alkyl groups, wherein each alkyl group may be the same or different.

The term halo as used herein means halogen and includes fluoro, chloro, bromo, iodo and the like, in both radioactive and non radioactive forms.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formulae I and II. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of a compound of Formula 1 or 2 are more soluble in water and various hydrophilic organic solvents, and generally demonstrate higher melting points in comparison to their free base forms. The selection criteria for the appropriate salt will be known to one skilled in the art. Other non-pharmaceutically acceptable salts, e.g. oxalates, may be used for example in the isolation of compounds of Formulae I and II for laboratory use, or for subsequent conversion to a pharmaceutically acceptable acid addition salt. It should be noted that compounds of Formulae I and II, wherein Z is N are not stable in the presence of strong acid (for example 1N HCl), therefore when preparing acid addition salts of such compounds, care must be taken to select an appropriately mild acid, for example citric acid.

A "pharmaceutically acceptable basic addition salt" is any non-toxic organic or inorganic base addition salt of the acid compounds represented by Formulae I and II. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. Those skilled in the art will appreciate that the selection of the appropriate salt may be important so that any ester functionality in the molecule is not hydrolyzed.

"Solvate" means a compound of Formula I or II or the pharmaceutically acceptable salt of a compound of Formula I or II wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "schizophrenia" means schizophrenia, schizophreniform disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The present invention includes within its scope prodrugs of the compounds of Formula I. In general, such prodrugs will be functional derivatives of the compounds of Formula I which are readily convertible in vivo into the required compound of Formula I. Conventional procedures for the selection and preparation of suitable prodrug derivatives are described, for example, in "Design of Prodrugs" ed. H. Bundgaard, Elsevier, 1985.

In embodiments of the invention, compounds of Formula I include those in which $R^1$, $R^2$, $R^3$ and $R^4$ are independently selected from the group consisting of H, halo, OH, $C_{1-6}$alkyl, $C_{1-6}$alkoxy, $C_{2-6}$alkenyl, $C_{2-6}$alkynyl, $C_{3-7}$cycloalkyl, $C_{4-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $NR^8R^9$, $C(O)NR^8R^9$, $SO_2NR^8R^9$, $CH_2SO_2NR^8R^9$, $CO_2R^{10}$, $NHC(O)R^{11}$, $NHC(NR^{12})R^{11}$, $C(NR^{13})NR^{14}R^{15}$, $C(O)R^{16}$, $OC(O)R^{16}$, $SCF_3$, $SO_2CF_3$, formyl, $CF_3$ and $CF_3O$. In other embodiments of the invention, three of $R^1$–$R^4$ are H and any one of $R^1$, $R^2$, $R^3$ and $R^4$ is independently selected from the group consisting of H, halo, OH, $C_{1-6}$alkyl, $C_{1-6}$alkoxy, $C_{2-6}$alkenyl, $C_{2-6}$alkynyl, $C_{3-7}$cycloalkyl, $C_{4-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $NR^8R^9$, $C(O)NR^8R^9$, $SO_2NR^8R^9$, $CH_2SO_2NR^8R^9$, $CO_2R^{10}$, $NHC(O)R^{11}$, $NHC(NR^{12})R^{11}$, $C(NR^{13})NR^{14}R^{15}$, $C(O)R^{16}$, $OC(O)R^{16}$, $SCF_3$, $SO_2CF_3$, formyl, $CF_3$ and $CF_3O$. In specific embodiments, it is $R^1$, $R^3$ and $R^4$ that are all H. In other specific embodiments, the compounds of the invention include those in which either:

(a) $R^1$–$R^4$ are all H;
(b) $R^1$ and $R^3$ are H and $R^2$ and $R^4$ are selected from halo, $C_{1-6}$alkyl, $C_{1-6}$alkoxy, $CF_3$ and $CF_3O$;
(c) $R^1$–$R^3$ are all H and $R^4$ is $C_{1-6}$alkyl; or
(d) $R^1$, $R^3$ and $R^4$ are all H and $R^2$ is selected from halo, $C_{1-6}$alkyl, $C_{1-6}$alkoxy, $CF_3$, $CF_3O$ and $C_{3-7}$cycloalkoxy.

In more specific embodiments, the compounds of the invention include those in which either:
(a) $R^1$–$R^4$ are all H;
(b) $R^1$ and $R^3$ are H and $R^2$ and $R^4$ are both fluoro;
(c) $R^1$, $R^3$ and $R^4$ are H and $R^2$ is selected from halo, $C_{1-6}$alkyl, $C_{1-6}$alkoxy and cyclohexyloxy; or
(d) $R^1$–$R^3$ are all H and $R^4$ is methyl.

In the most specific embodiments, the compounds of the invention include those where $R^1$, $R^3$ and $R^4$ are H and $R^2$ is selected from fluoro, methyl and methoxy.

In further embodiments, when one or more of $R^1$–$R^4$ is selected from $NR^8R^9$, $C(O)NR^8R^9$, $SO_2NR^8R^9$, $CH_2SO_2NR^8R^9$ and $CO_2R^{10}$ Formula I, $R^8$, $R^9$ and $R^{10}$ are independently selected from the group consisting of H, $C_{1-6}$alkyl and phenyl or $R^8$ and $R^9$ may form an alkylene chain, $—(CH_2)_n—$, where n=3–6, to form, together with the nitrogen to which they are attached a 4-to 7-membered ring. In specific embodiments, $R^8$, $R^9$ and $R^{10}$ are independently selected from the group consisting of H and $C_{1-4}$alkyl or $R^8$ and $R^9$ may form an alkylene chain, $—(CH_2)_n—$, where n=4–5, to form, together with the nitrogen to which they are attached a 5- to 6-membered ring. In more specific embodiments, $R^8$, $R^9$ and $R^{10}$ are independently selected from the group consisting of H and methyl or $R^8$ and $R^9$ may form an alkylene chain, $—(CH_2)_n—$, where n=4–5, to form, together with the nitrogen to which they are attached a 5- to 6-membered ring.

In other embodiments, when one or more of $R^1$–$R^4$ is selected from $NHC(O)R^{11}$, $NHC(NR^{12})R^{11}$ in compounds of Formula I, $R^{11}$ is selected from $C_{1-6}$alkyl, $C_{1-6}$alkoxy, phenyl, phenoxy, $NH_2$, alkylamino, dialkylamino, benzyl and benzyloxy and $R^{12}$ is selected from the group consisting of H and $C_{1-6}$alkyl. In specific embodiments, $R^{11}$ is selected from $C_{1-4}$alkyl, $C_{1-4}$alkoxy, phenyl, phenoxy, $NH_2$, alkylamino, dialkylamino, benzyl and benzyloxy and $R^{12}$ is selected from the group consisting of H and $C_{1-4}$alkyl. In more specific embodiments, $R^{11}$ is selected from methyl, methoxy, phenyl, phenoxy, $NH_2$, alkylamino, dialkylamino, benzyl and benzyloxy and $R^{12}$ is selected from the group consisting of H and methyl. Further, when one or more of $R^1$–$R^4$ is $C(NR^{13})NR^{14}R^{15}$ in compounds of Formula I, $R^{13}$ is selected from the group consisting of H and $C_{1-6}$alkyl and $R^{14}$ and $R^{15}$ are independently selected from the group consisting of H and $C_{1-6}$alkyl or one of $R^{14}$ and $R^{15}$, together with $R^{13}$, forms an alkylene chain, $—(CH_2)_n—$, where n=2 or 3, bridging the nitrogen atoms to which they are attached. In specific embodiments, $R^{13}$ is selected from the group consisting of H and $C_{1-4}$alkyl and $R^{14}$ and $R^{15}$ are independently selected from the group consisting of H and $C_{1-4}$alkyl or one of $R^{14}$ and $R^{15}$, together with $R^{13}$, forms an alkylene chain, $—(CH_2)_n—$, where n=2 or 3, bridging the nitrogen atoms to which they are attached. In more specific embodiments, $R^{13}$ is selected from the group consisting of H and methyl and $R^{14}$ and $R^{15}$ are independently selected from the group consisting of H and methyl or one of $R^{14}$ and $R^{15}$, together with $R^{13}$, forms an alkylene chain, $—(CH_2)_n—$, where n=3, bridging the nitrogen atoms to which they are attached. Finally, when one or more of $R^1$–$R^4$ is selected from $C(O)R^{16}$ and $OC(O)R^{16}$ in compounds of Formula I, $R^{16}$ is selected from the group consisting of optionally substituted phenyl, optionally substituted pyridyl, optionally substituted thienyl, optionally substituted furanyl and optionally substituted naphthyl. Specifically, $R^{16}$ is selected from the group consisting of optionally substituted phenyl and optionally substituted naphthyl. More specifically, $R^{16}$ is selected from the group consisting of unsubstituted phenyl and unsubstituted naphthyl.

In another embodiment of the invention, compounds of Formula I include those in which $R^6$ is independently selected from the group consisting of H, $C_{1-6}$alkyl, optionally substituted phenyl and optionally substituted benzyl, and $R^7$ is independently selected from the group consisting of H, $C_{1-6}$alkyl, $C_{1-6}$alkoxy, $C_{1-6}$alkylthio, optionally substituted phenyl, optionally substituted benzyl, optionally substituted phenoxy and optionally substituted benzyloxy. In specific embodiments, $R^6$ is selected from H and $C_{1-4}$alkyl and $R^7$ is selected from H, $C_{1-4}$alkyl, $C_{1-4}$alkoxy and $C_{1-4}$alkylthio. In more specific embodiments, $R^6$ and $R^7$ are both H.

Compounds of Formula I, also include those in which X is selected from the group consisting of $CR^{17}$ and N, wherein $R^{17}$ is selected from the group consisting of H, $C_{1-6}$alkyl and benzyl. In specific emdodiments, X is selected from $CR^{17}$ and N, wherein $R^{17}$ is selected from the group consisting of H, and $C_{1-4}$alkyl. In more specific embodiments, X is CH.

In another embodiment of the invention, Z is selected from C, CH and N, ───── represents a single or double bond (provided there is only one double bond in the ring at a time) and n is an integer of from 1 to 3. In specific embodiments, Z is selected from C, CH and N, ───── represents a single or double bond and n is an integer of from 1 to 2. In more specific embodiments, Z, ───── and n are selected to form a ring system selected from 1,4-diaza[4.3.0]bicyclononane, 1,4-diaza[4.4.0]bicyclodecane, 1,2,3,5,8,8a-hexahydroindolizine, 1,2,3,5,6,8a-hexahydroindolizine and octahydroindolizine. In the most specific embodiments, Z, ───── and n are selected to form a ring system selected from 1,4-diaza[4.4.0]bicyclodecane, 1,2,3,5,8,8a-hexahydroindolizine and octahydroindolizine.

Compounds of the invention further include those in which $R^5$ is selected from the group consisting of $SO_2Ar$, $C(O)Ar$, $CH_2Ar$ and Ar, wherein Ar is an optionally substituted aromatic group selected from the group consisting of phenyl, pyridyl, thienyl, furanyl, naphthyl, quinolyl and isoquinolyl wherein the optional substituents are independently selected from 1–4 members of the group consisting of halo, OH, $C_{1-6}$alkyl, $C_{1-6}$alkoxy, $C_{1-6}$alkylthio, $CF_3$ and $CF_3O$. In specific embodiments of the invention, $R^5$ is selected from $SO_2Ar$, $C(O)Ar$, $CH_2Ar$ and Ar, most specifically $SO_2Ar$, wherein Ar is selected from phenyl and naphthyl. When Ar is phenyl, it is specifically unsubstituted or substituted with 1–3 substituents optionally selected from $C_{1-6}$alkyl, halo and $C_{1-6}$alkoxy. When Ar is naphthyl, it is specifically unsubstituted naphthyl. More specifically, when Ar is phenyl, it is either unsubstituted or substituted with 1–3 substituents independently selected from $C_{1-4}$alkyl, $C_{1-6}$alkoxy and halo. Most specifically Ar is selected from phenyl, 1-naphthyl, 2-naphthyl, 4-halophenyl, 4-($C_{1-4}$alkyl)phenyl, 4-($C_{1-4}$alkoxy)phenyl, 2,5-dihalophenyl, 2-halophenyl, 3-($C_{1-4}$alkyl)phenyl, 2,6-dihalophenyl and 2,4,6-tri-($C_{1-4}$alkyl)phenyl. Even more specifically, Ar is selected from phenyl, 4-halophenyl, 4-($C_{1-4}$alkyl)phenyl, 4-($C_{1-4}$alkoxy)phenyl, 1-naphthyl and 2-naphthyl. Most specifically, Ar is selected from phenyl, 1-naphthyl and 2-naphthyl.

In a further embodiment of the invention, compounds of Formula I encompass those in which halo is selected from non-radioactive halo and radioactive halo. When halo is radioactive halo, it may be, for example, radioactive iodo.

Specific compounds of Formula I include:

3-[(6-R,S)-1,4-Diaza[4.3.0]bicyclonon-4-yl)]-1-(2-naphthalenesulfonyl)indole;

3-[(6-R,S)-1,4-Diaza[4.3.0]bicyclonon-4-yl]-1-(1-naphthalenesulfonyl)indole;
1-(4-Bromophenylsulfonyl)-3-[(6-R,S)-1,4-diaza[4.3.0]bicyclonon-4-yl]indole;
1-(4-t-Butylphenylsulfonyl)-3-[(6-R,S)-1,4-diaza[4.3.0]bicyclonon-4-yl]indole;
1-(4-Chlorophenylsulfonyl)-3-[(6-R,S)-1,4-diaza[4.3.0]bicyclonon-4-yl]indole;
3-[(6-R,S)-1,4-Diaza[4.3.0]bicyclonon-4-yl]-1-(4-fluorophenylsulfonyl)indole;
3-[(6-R,S)-1,4-Diaza[4.3.0]bicyclonon-4-yl]-1-(4-methoxyphenylsulfonyl)indole;
3-[(6-R,S)-1,4-Diaza[4.3.0]bicyclonon-4-yl]-1-(2,5-dichlorophenylsulfonyl)indole;
1-(2-Bromophenylsulfonyl)-3-[(6-R,S)-1,4-diaza[4.3.0]bicyclonon-4-yl]indole;
3-[(6-R,S)-1,4-Diaza[4.3.0]bicyclonon-4-yl]-1-(phenylsulfonyl)indole;
3-[(6-R,S)-1,4-Diaza[4.3.0]bicyclonon-4-yl]-1-(4-methylphenylsulfonyl)indole;
3-[(6-R,S)-1,4-Diaza[4.4.0]bicyclodecan-4-yl]-1-(2-naphthalenesulfonyl)indole;
3-[(6-R,S)-1,4-Diaza[4.4.0]bicyclodecan-4-yl]-1-(1-naphthalenesulfonyl)indole;
1-(4-Bromophenylsulfonyl)-3-[(6-R,S)-1,4-diaza[4.4.0]bicyclodecan-4-yl]indole;
1-(4-t-Butylphenylsulfonyl)-3-[(6-R,S)-1,4-diaza[4.4.0]bicyclodecan-4-yl]indole;
1-(4-Chlorophenylsulfonyl)-3-[(6-R,S)-1,4-diaza[4.4.0]bicyclodecan-4-yl]indole;
3-[(6-R,S)-1,4-Diaza[4.4.0]bicyclodecan-4-yl]-1-(4-fluorophenylsulfonyl)indole;
3-[(6-R,S)-1,4-Diaza[4.4.0]bicyclodecan-4-yl]-1-(4-methoxyphenylsulfonyl)indole;
3-[(6-R,S)-1,4-Diaza[4.4.0]bicyclodecan-4-yl]-1-(2,5-dichlorophenylsulfonyl)indole;
1-(2-Bromophenylsulfonyl)-3-[(6-R,S)-1,4-diaza[4.4.0]bicyclodecan-4-yl]indole;
3-[(6-R,S)-1,4-Diaza[4.4.0]bicyclodecan-4-yl]-1-(phenylsulfonyl)indole;
3-[(6-R,S)-1,4-Diaza[4.4.0]bicyclodecan-4-yl]-1-(4-methylphenylsulfonyl)indole;
3-[(6-R,S)-1,4-Diaza[4.4.0]bicyclodecan-4-yl]-1-(2,4,6-trimethylphenylsulfonyl)indole;
5-Fluoro-3-[(8a-R,S)-1,2,3,5,8,8a-hexahydro-7-indolizinyl]-1-phenylsulfonylindole;
5-Fluoro-3-[(8a-R,S)-1,2,3,5,8,8a-hexahydro-7-indolizinyl]-1-(1-naphthalenesulfonyl)indole;
5-Fluoro-3-[(8a-R,S)-1,2,3,5,8,8a-hexahydro-7-indolizinyl]-1-(2-naphthalenesulfonyl)indole;
5-Fluoro-1-(4-fluorophenylsulfonyl)-3-[(8a-R,S)-1,2,3,5,8,8a-hexahydro-7-indolizinyl]indole;
1-(4-Bromophenylsulfonyl)-5-fluoro-3-[(8a-R,S)-1,2,3,5,8,8a-hexahydro-7-indolizinyl]indole;
1-(2-Bromophenylsulfonyl)-5-fluoro-3-[(8a-R,S)-1,2,3,5,8,8a-hexahydro-7-indolizinyl]indole;
5-Fluoro-3-[(8a-R,S)-1,2,3,5,8,8a-hexahydro-7-indolizinyl]-1-(4-methylphenylsulfonyl)indole;
5-Fluoro-3-[(8a-R,S)-1,2,3,5,8,8a-hexahydro-7-indolizinyl]-1-(4-methoxyphenylsulfonyl)indole;
5-Fluoro-3-[(8a-R,S)-1,2,3,5,8,8a-hexahydro-7-indolizinyl]-1-(2,4,6-trimethylphenylsulfonyl)indole;
1-(4-t-Butylphenylsulfonyl)-5-fluoro-3-[(8a-R,S)-1,2,3,5,8,8a-hexahydro-7-indolizinyl]indole;
1-(2,5-Dichlorophenylsulfonyl)-5-fluoro-3-[(8a-R,S)-1,2,3,5,8,8a-hexahydro-7-indolizinyl]indole;
1-(4-Chlorophenylsulfonyl)-5-fluoro-3-[(8a-R,S)-1,2,3,5,8,8a-hexahydro-7indolizinyl]indole;

3-[(6-R,S)-1,4-Diaza[4.3.0]bicyclonon-4-yl]-1-(4-methylphenylsulfonyl)indazole;
3-[(6-R,S)-1,4-Diaza[4.4.0]bicyclodecan-4-yl]-1-(4-methylphenylsulfonyl)indazole;
5,7-Difluoro-3-[(8a-R,S)-1,2,3,5,8,8a-hexahydro-7-indolizinyl]-1-phenylsulfonylindole;
5,7-Difluoro-3-[(8a-R,S)-1,2,3,5,8,8a-hexahydro-7-indolizinyl]-1-naphthalenesulfonylindole;
5,7-Difluoro-3-[(8a-R,S)-1,2,3,5,8,8a-hexahydro-7-indolizinyl]-2-naphthalenesulfonylindole;
5-Methoxy-3-[(8a-R,S)-1,2,3,5,8,8a-hexahydro-7-indolizinyl]-1-phenylsulfonylindole;
5-Methoxy-3-[(8a-R,S)-1,2,3,5,8,8a-hexahydro-7-indolizinyl]-1naphthalenesulfonylindole;
5-Methoxy-3-[(8a-R,S)-1,2,3,5,8,8a-hexahydro-7-indolizinyl]-2-naphthalenesulfonylindole;
5-Methyl-3-[(8a-R,S)-1,2,3,5,8,8a-hexahydro-7-indolizinyl]-1-phenylsulfonylindole;
5-Methyl-3-[(8a-R,S)-1,2,3,5,8,8a-hexahydro-7-indolizinyl]-1-naphthalenesulfonylindole;
5-Methyl-3-[(8a-R,S)-1,2,3,5,8,8a-hexahydro-7-indolizinyl]-2-naphthalenesulfonylindole;
7-Methyl-3-[(8a-R,S)-1,2,3,5,8,8a-hexahydro-7-indolizinyl]-1-phenylsulfonylindole;
7-Methyl-3-[(8a-R,S)-1,2,3,5,8,8a-hexahydro-7-indolizinyl]-1-naphthalenesulfonylindole;
7-Methyl-3-[(8a-R,S)-1,2,3,5,8,8a-hexahydro-7-indolizinyl]-2-naphthalenesulfonylindole;
5-Fluoro-3-(1,2,3,5,8,8a-hexahydrohydro-7-indolizinyl)-1-(3-methylphenyl)indole;
5-Fluoro-3-[(7-R,S)(8a-R,S)-octahydro-7-indolizinyl]-1-(3-methylphenyl)indole;
5-Fluoro-3-[(7R or 7S)(8a-R,S)-octahydrohydro-7-indolizinyl]-1-(2-naphthalenesulfonyl)indole, Isomer I;
5-Fluoro-3-[(7R or 7S)(8a-R,S)-octahydrohydro-7-indolizinyl]-1-(2-naphthalenesulfonyl)indole, Isomer II;
5-Fluoro-3-[(7R or 7S)(8a-R,S)-octahydrohydro-7-indolizinyl]-1-phenylsulfonylindole, Isomer I;
5-Fluoro-3-[(7R or 7S)(8a-R,S)-octahydrohydro-7-indolizinyl]-1-phenylsulfonylindole, Isomer II;
5-Fluoro-3-[(7R or 7S)(8a-R,S)-octahydrohydro-7-indolizinyl]-1-(1-naphthalenesulfonyl)indole, Isomer I;
5-Fluoro-3-[(7R or 7S)(8a-R,S)-octahydrohydro-7-indolizinyl]-1-(1-naphthalenesulfonyl)indole, Isomer II;
5-Fluoro-3-[(7R or 7S)(8a-R,S)-octahydrohydro-7-indolizinyl]-1-(2,6-dichloro-benzoyl)indole, Isomer I;
1-Benzyl-5-fluoro-3-[(7R or 7S)(8a-R,S)-octahydrohydro-7-indolizinyl]indole, Isomer I;
5-Cyclohexyloxy-3-[(8a-R,S)-1,2,3,5,8,8a-hexahydrohydro-7-indolizinyl]-1-phenylsulfonylindole;
1-(2,5-Dichlorophenylsulfonyl)-5-Fluoro-3-[(7R or 7S)(8a-R,S)-octahydrohydro-7-indolizinyl]indole, Isomer I;
5-Fluoro-1-(3-methylphenylsulfonyl)-3-[(7R or 7S)(8a-R,S) octahydrohydro-7-indolizinyl]]indole, Isomer I;
1-(2-Chlorobenzoyl)-5-fluoro-3-[(8a-R,S)-1,2,3,5,8,8a-hexahydro-7-indolizinyl)indole;
5-Fluoro-1-[1-(2-naphthyl)methyl]-3-[(7R or 7S)(8a-R,S)-octahydro-7-indolizinyl)indole, Isomer I;
5-Fluoro-1-(1-naphthoyl)-3-[(7R or 7S)(8a-R,S)-octahydro-7-indolizinyl]indole, Isomer I; and
5-Fluoro-1-[1-(1-naphthyl)methyl]-3-[(7R or 7S)(8a-R,S)-octahydro-7-indolizinyl]indole, Isomer I.

In specific embodiments of the invention, the compounds of Formula I include:

3-[(6-R,S)-1,4-Diaza[4.3.0]bicyclonon-4-yl]-1-(2-naphthalenesulfonyl)indole;
3-[(6-R,S)-1,4-Diaza[4.3.0]bicyclonon-4-yl]-1-(1-naphthalenesulfonyl)indole;
1-(4-Bromophenylsulfonyl)-3-[(6-R,S)-1,4-diaza[4.3.0]bicyclonon-4-yl]indole;
1-(4-t-Butylphenylsulfonyl)-3-[(6-R,S)-1,4-diaza[4.3.0]bicyclonon-4-yl]indole;
3-[(6-R, S)-1,4-Diaza[4.3.0]bicyclonon-4-yl]-1-(4-methoxyphenylsulfonyl)indole;
3-[(6-R,S)-1,4-Diaza[4.3.0]bicyclonon-4-yl]-1-(phenylsulfonyl)indole;
3-[(6-R,S)-1,4-Diaza[4.3.0]bicyclonon-4-yl]-1-(4-methylphenylsulfonyl)indole;
3-[(6-R,S)-1,4-Diaza[4.4.0]bicyclodecan-4-yl]-1-(2-naphthalenesulfonyl)indole;
3-[(6-R,S)-1,4-Diaza[4.4.0]bicyclodecan-4-yl]-1-(1-naphthalenesulfonyl)indole;
1-(4-Bromophenylsulfonyl)-3-[(6-R,S)-1,4-diaza[4.4.0]bicyclodecan-4-yl]indole;
1-(4-Chlorophenylsulfonyl)-3-[(6-R,S)-1,4-diaza[4.4.0]bicyclodecan-4-5yl]indole;
3-[(6-R,S)-1,4-Diaza[4.4.0]bicyclodecan-4-yl]-1-(phenylsulfonyl)indole;
3-[(6-R,S)-1,4-Diaza[4.4.0]bicyclodecan-4-yl]-1-(4-methylphenylsulfonyl)indole;
5-Fluoro-3-[(8a-R,S)-1,2,3,5,8,8a-hexahydro-7-indolizinyl]-1-phenylsulfonylindole;
5-Fluoro-3-[(8a-R,S)-1,2,3,5,8,8a-hexahydro-7-indolizinyl]-1-(1-naphthalenesulfonyl)indole;
5-Fluoro-3-[(8a-R,S)-1,2,3,5,8,8a-hexahydro-7-indolizinyl]-1-(2-naphthalenesulfonyl)indole;
5-Fluoro-1-(4-fluorophenylsulfonyl)-3-[(8a-R,S)-1,2,3,5,8,8a-hexahydro-7-indolizinyl]indole;
1-(4-Bromophenylsulfonyl)-5-fluoro-3-[(8a-R,S)-1,2,3,5,8,8a-hexahydro-7-indolizinyl]indole;
1-(2-Bromophenylsulfonyl)-5-fluoro-3-[(8a-R,S)-1,2,3,5,8,8a-hexahydro-7-indolizinyl]indole;
5-Fluoro-3-[(8a-R,S)-1,2,3,5,8,8a-hexahydro-7-indolizinyl]-1-(4-methylphenylsulfonyl)indole;
5-Fluoro-3-[(8a-R,S)-1,2,3,5,8,8a-hexahydro-7-indolizinyl]-1-(4-methoxyphenylsulfonyl)indole;
1-(4-t-Butylphenylsulfonyl)-5-fluoro-3-[(8a-R,S)-1,2,3,5,8,8a-hexahydro-7-indolizinyl]indole;
1-(2,5-Dichlorophenylsulfonyl)-5-fluoro-3-[(8a-R,S)-1,2,3,5,8a-hexahydro-7-indolizinyl]indole;
1-(4-Chlorophenylsulfonyl)-5-fluoro-3-[(8a-R,S)-1,2,3,5,8,8a-hexahydro-7-indolizinyl]indole;
5,7-Difluoro-3-[(8a-R,S)-1,2,3,5,8,8a-hexahydro-7-indolizinyl]-1-phenylsulfonylindole;
5,7-Difluoro-3-[(8a-R,S)-1,2,3,5,8,8a-hexahydro-7-indolizinyl]-1-naphthalenesulfonylindole;
5,7-Difluoro-3-[(8a-R,S)-1,2,3,5,8,8a-hexahydro-7-indolizinyl]-2-naphthalenesulfonylindole;
5-Methoxy-3-[(8a-R,S)-1,2,3,5,8,8a-hexahydro-7-indolizinyl]-1-phenylsulfonylindole;
5-Methoxy-3-[(8a-R,S)-1,2,3,5,8,8a-hexahydro-7-indolizinyl]-1-naphthalenesulfonylindole;
5-Methoxy-3-[(8a-R,S)-1,2,3,5,8,8a-hexahydro-7-indolizinyl]-2-naphthalenesulfonylindole;
5-Methyl-3-[(8a-R,S)-1,2,3,5,8,8a-hexahydro-7-indolizinyl]-1-phenylsulfonylindole;
5-Methyl-3-[(8a-R,S)-1,2,3,5,8,8a-hexahydro-7-indolizinyl]-1-naphthalenesulfonylindole;
5-Methyl-3-[(8a-R,S)-1,2,3,5,8,8a-hexahydro-7-indolizinyl]-2-naphthalenesulfonylindole;
7-Methyl-3-[(8a-R,S)-1,2,3,5,8,8a-hexahydro-7-indolizinyl]-1-phenylsulfonylindole;
7-Methyl-3-[(8a-R,S)-1,2,3,5,8,8a-hexahydro-7-indolizinyl]1-naphthalenesulfonylindole;

5-Fluoro-3-[(7R or 7S)(8a-R,S)-octahydrohydro-7-indolizinyl]-1-(2-naphthalenesulfonyl)indole, Isomer II; and 5-Fluoro-3-[(7R or 7S)(8a-R,S)-octahydrohydro-7-indolizinyl]-1-(1-naphthalenesulfonyl)indole, Isomer II.

In more specific embodiments of the invention, the compounds of Formula I include:

3-[(6-R,S)-1,4-Diaza[4.4.0]bicyclodecan-4-yl]-1-(1-naphthalenesulfonyl)indole;

5-Fluoro-3-[(8a-R,S)-1,2,3,5,8,8a-hexahydro-7-indolizinyl]-1-phenylsulfonylindole;

5-Fluoro-3-[(8a-R,S)-1,2,3,5,8,8a-hexahydro-7-indolizinyl]-1-(2-naphthalenesulfonyl)indole;

5,7-Difluoro-3-[(8a-R,S)-1,2,3,5,8,8a-hexahydro-7-indolizinyl]-2-naphthalenesulfonylindole;

5-Methoxy-3-[(8a-R,S)-1,2,3,5,8,8a-hexahydro-7-indolizinyl]-1-phenylsulfonylindole;

5-Methoxy-3-[(8a-R,S)-1,2,3,5,8,8a-hexahydro-7-indolizinyl]-1-naphthalenesulfonylindole;

5-Methoxy-3-[(8a-R,S)-1,2,3,5,8,8a-hexahydro-7-indolizinyl]-2-naphthalenesulfonylindole;

5-Methyl-3-[(8a-R,S)-1,2,3,5,8,8a-hexahydro-7-indolizinyl]-1-phenylsulfonylindole;

5-Methyl-3-[(8a-R,S)-1,2,3,5,8,8a-hexahydro-7-indolizinyl]-1-naphthalenesulfonylindole;

5-Methyl-3-[(8a-R,S)-1,2,3,5,8,8a-hexahydro-7-indolizinyl]-2-naphthalenesulfonylindole;

5,7-Difluoro-3-[(8a-R,S)-1,2,3,5,8,8a-hexahydro-7-indolizinyl]-1-phenylsulfonylindole; and 5-Fluoro-3-[(7R or 7S)(8a-R,S)-octahydrohydro-7-indolizinyl]-1-(2-naphthalenesulfonyl)indole, Isomer II.

All of the compounds of Formulae I and II have at least one asymmetric centre. Where the compounds according to the invention have one asymmetric centre they may exist as enantiomers. Where the compounds according to the invention possess two or more asymmetric centres, they may additionally exist as diastereomers. It is to be understood that all such isomers and mixtures thereof in any proportion are encompassed within the scope of the present invention.

The conversion of a given compound salt to a desired compound salt is achieved by applying standard techniques, in which an aqueous solution of the given salt is treated with either a solution of a base e.g. sodium carbonate or potassium hydroxide, or an acid, e.g. HCl (caution when Z=N), to liberate the neutral compound which is then extracted into an appropriate solvent, such as ether. The neutral compound is then separated from the aqueous portion, dried, and treated with the requisite acid or base to give the desired salt.

Also included within the scope of the invention are solvates of the invention. The formation of the solvate will vary depending on the compound and solvent used. In general, solvates are formed by dissolving the compound in the appropriate solvent and isolating the solvate by cooling or using an antisolvent. The solvate is typically dried or azeotroped under ambient conditions.

Prodrugs of compounds of Formula I may be conventional esters with available hydroxyl (or thiol) or carboxyl groups. For example, when one of $R^1$–$R^7$ is or contains a hydroxyl group in a compound of Formula I, it may be acylated using an activated acid in the presense of a base and, optionally, in inert solvent (e.g. an acid chloride in pyridine). Also, when one of $R^1$–$R^4$ is $CO_2R^{10}$ in a compound of Formula I, wherein $R^{10}$ is H, an ester may be formed by activation of the hydroxyl group of the acid and treatment with the appropriate alcohol in the presence of a base in an inert solvent. Some common esters which have been utilized as prodrugs are phenyl esters, aliphatic ($C_1$–$C_{24}$) esters, acyloxymethyl esters, carbamates and amino acid esters. Prodrugs of compounds of Formula I may also be formed by functional derivatization of substituents containing an acidic NH group, for example, compounds of Formula I, where one of $R^1$–$R^4$ $C(O)NR^8R^9$, $SO_2NR^8R^9$, $NHC(NR^{12})R^{11}$ or $C(NR^{13})NR^{14}R^{15}$ and one of the groups attached to a nitrogen is H. Some common prodrugs for amides, imides and other NH-acidic compounds are N-Mannich bases, N-hydroxymethyl derivatives, N-acyloxyalkyl derivatives, and N-acyl derivatives.

In accordance with other aspects of the invention, the compounds of the present invention can be prepared by processes analogous to those established in the art. For example, as shown in Scheme 1, compounds of Formula I, wherein $R^5$ is selected from $SO_2Ar$, $C(O)Ar$ and $CH_2Ar$, may be prepared by first treating compounds of Formula II, wherein $R^1$–$R^4$, $R^5$ is H, $R^6$, $R^7$, n, —————, X and Z are as defined in Formula I, with a suitable base, followed by the addition of a reagent of either Formula B, C or D, wherein Ar is as defined in Formula I and Y is a suitable leaving group such as halo, arylsulfonyloxy or alkylsulfonyloxy, preferably bromo or chloro, to provide compounds of Formula I wherein $R^5$ is $C(O)Ar$, $SO_2Ar$ or $CH_2Ar$, respectively. Therefore, for example, treatment of compounds of Formula A with a strong base such as lithium diisopropylamide, n-butyllithium or sodium bis(trimethylsilyl)amide in an inert solvent such as tetrahydrofuran or hexanes at a temperature in the range of −100 to 30° C. or, alternatively an organic amine in the presence of 4-dimethylaminopyridine (DMAP), in an inert solvent such as methylene chloride or chloroform, at a temperature in the range of 0–60°C., followed by the addition of reagents of Formula B, C or D, provides compounds of Formula I, wherein $R^5$ is $C(O)Ar$, $SO_2Ar$ or $CH_2Ar$ respectively. Preferred conditions are sodium bis(trimethylsilyl)amide in tetrahydrofuran at teperatures in the range of 0° C. to room temperature or triethylamine and DMAP in methylene chloride at room temperature. Reagents B, C D are commercially available or can be prepared using standard methods known to those skilled in the art. The preparation of compounds of Formula II is described below.

Scheme 1

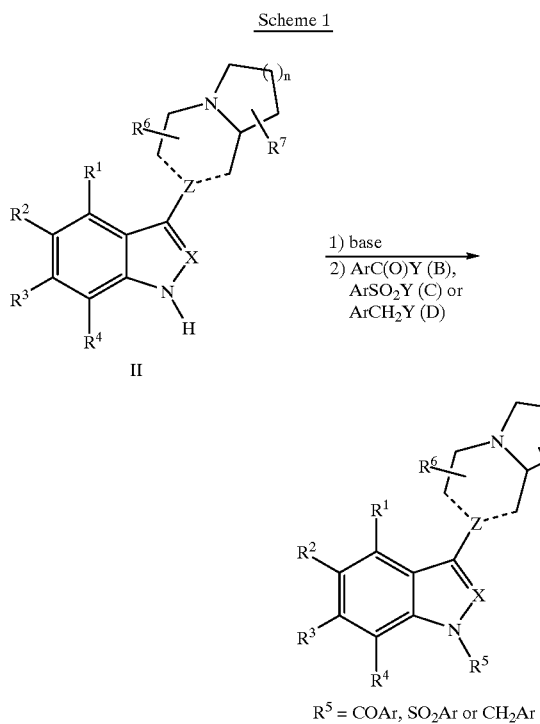

As shown in Scheme 2, compounds of Formula I wherein R⁵ is Ar may be prepared by treating compounds of Formula II, wherein R¹–R⁴, R⁵ is H, R⁶, R⁷, n, ——————, X and Z are as defined in Formula I, with an arylhalide of Formula E, wherein Ar is as defined in Formula I and Hal is selected from I, Br and Cl, under standard Ullmann arylation conditions, for example in the presence of a base such as potassium carbonate and a catalyst such as copper, copper (I) iodide or copper (I) bromide or mixtures thereof, in an inert solvent such as N-methylpyrrolidinone (NMP), dimethylformamide (DMF), hexamethylphosphoramide (HMPA) or dimethylsulfoxide (DMSO) at temperatures in the range of 150–200 ° C. Preferred conditions are copper (I) bromide and copper in NMP at temperatures in the range of 160–170° C.

Scheme 2

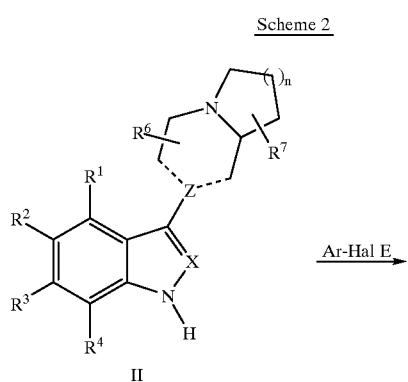

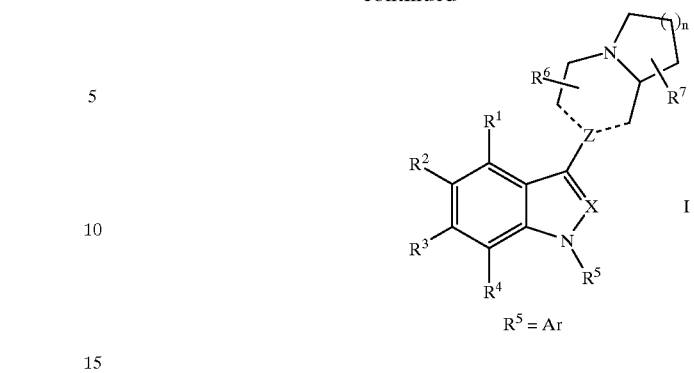

Compounds of Formula II are available by deprotecting compounds of Formula F, wherein R¹–R⁴, R⁶, R⁷, n, ——————, X and Z are as defined in Formula I and PG is a suitable protecting group, using standard deprotection conditions as shown in Scheme 3. When X is CR¹⁷, PG is preferably acetate which can be hydrolyzed under basic or acidic, preferably basic, conditions, for example sodium hydroxide in methanol at temperatures in the range of −20–100° C., suitably −10–80° C. When X is N, PG is preferably tosyl which can be removed under acidic conditions, for example HBr in acetic acid. It should be understood that the criteria for selection of a suitable protecting group would be known to a person skilled in the art as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley & Sons, 1991.

Scheme 3

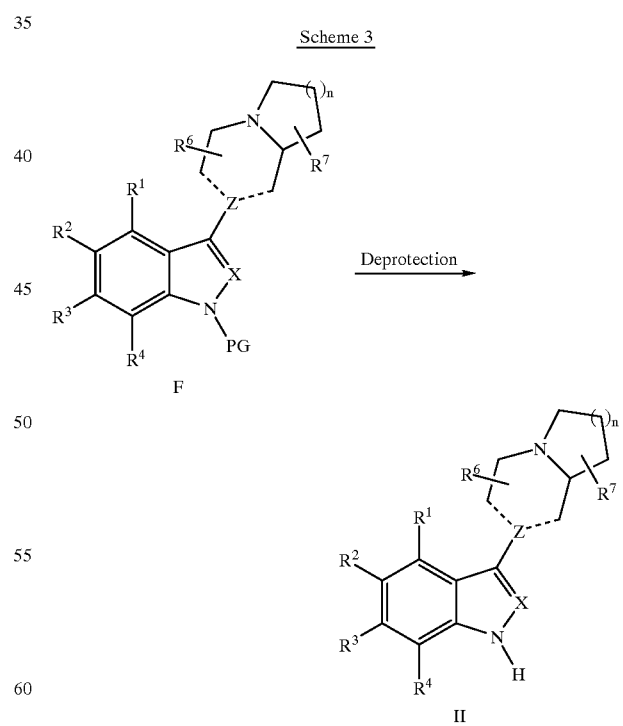

Compounds of Formula F, wherein R¹–R⁴, R⁶, R⁷ and n are as defined in Formula I, X is CR¹⁷, wherein R¹⁷ is as defined in Formula I, —————— is either a single or a double bond, Z is C or CH and PG is a suitable protecting group (Formulae F(a) and F(b)), may be prepared as shown in Scheme 4. A compound of Formula G, wherein $R^1$–$R^4$ are as defined in Formula I, may be condensed with a reagent of Formula H, wherein $R^6$, $R^7$ and n are as defined in Formula I, either in acidic or basic conditions, in a suitable solvent at temperatures in the range of 25–100° C., preferably, 60–90° C., to provide compounds of Formula F(a) and F(a)' wherein $R^1$–$R^4$, $R^6$, $R^7$ and n are as defined in Formula I. Suitable basic conditions include organic amines such as pyrrolidine or triethylamine in solvents such as methanol, ethanol and the like. Preferred basic conditions are pyrrolidine in ethanol at a refluxing temperature. Suitable acidic conditions include, for example, trifluoroacetic acid in acetic acid at a temperature in the range of 90–120° C., preferably at around 110° C. When the reaction of compound G with compound H is carried out in basic conditions, typically the regioisomer corresponding to F(a) is the sole product isolated. Under acidic conditions, both regioisomeric alkenes, F(a) and F(a)' may be isolated, the ratio of which will vary depending on reaction conditions and the identity and position of $R^6$. When $R^6$ is H, this ratio is typically 1:1. Compounds of Formula F(a) and F(a)', wherein $R^1$–$R^4$, $R^6$, $R^7$ and n are as defined in Formula I, may be reduced using standard hydrogenation conditions or using metal hydride reducing reagents to provide compounds of Formula F(b) where $R^1$–$R^4$, $R^6$, $R^7$ and n are as defined in Formula I, as shown in Scheme 4. Preferred is reduction by hydrogenation, using a suitable catalyst such as palladium or platinum on carbon in methanol or ethanol at room temperature. It should be noted that, in the series of reactions described above, the presence of the protecting group PG, is not always necessary, therefore compounds of Formula II could be obtained directly from compounds of Formula G where PG is replaced with H.

Scheme 4

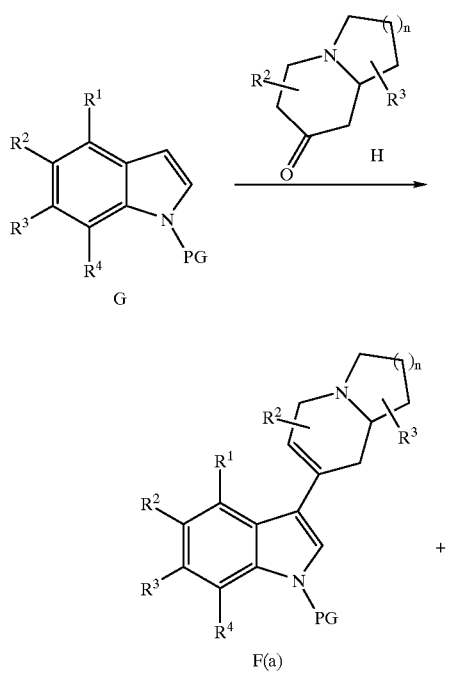

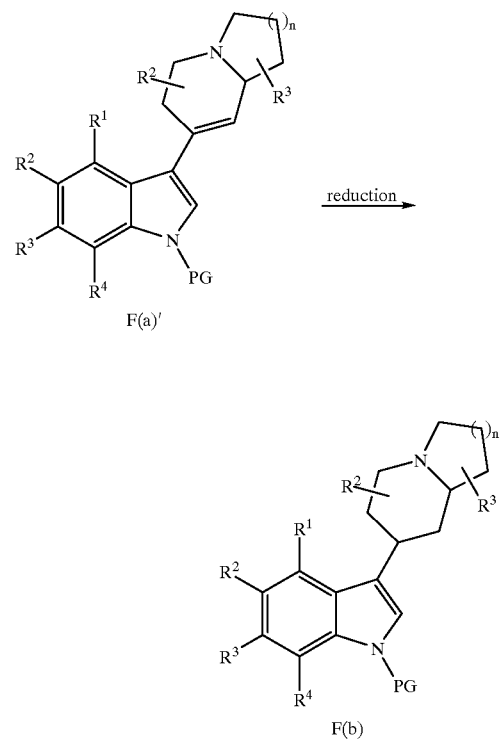

Compounds of Formula F, wherein $R^1$–$R^4$, $R^6$, $R^7$, and n are as defined in Formula I, ——— is either a single or a double bond, Z is C and X is N (Formulae F(c) and F(d)) may be prepared as shown in Scheme 5. A compound of Formula J, wherein $R^1$–$R^4$ are as defined in Formula I, PG is a suitable protecting group, such as tosylate, and Y is a leaving group such as halo, preferably chloro, can be reacted under standard palladium-catalyzed cross-coupling conditions with, for example, compounds of Formula K and K', wherein $R^6$, $R^7$ and n are as defined in Formula I and R is $C_{1-4}$alkyl, to provide compounds of Formula F(c) and F(c)', wherein $R^1$–$R^4$, $R^6$, $R^7$ and n are as defined in Formula I. It will be appreciated that other metal coupling reagents could be used in place of the stannane, for example, boronic acid, chloro zinc and the like. Preferred coupling conditions include refluxing the indazole and heterocyclic metal reagent in an inert solvent such as dimethylformamide, tetrahydrofuran or toluene in the presence of tetrakis (triphenylphosphine) palladium (0). Compounds of Formula F(c) and F(c)', wherein $R^1$–$R^4$, $R^6$, $R^7$ and n are as defined in Formula I, may be reduced using standard hydrogenation conditions or using metal hydride reducing reagents as decribed above to provide compounds of Formula F(d), wherein $R^1$–$R^4$, $R^6$, $R^7$ and n are as defined in Formula I.

Scheme 5

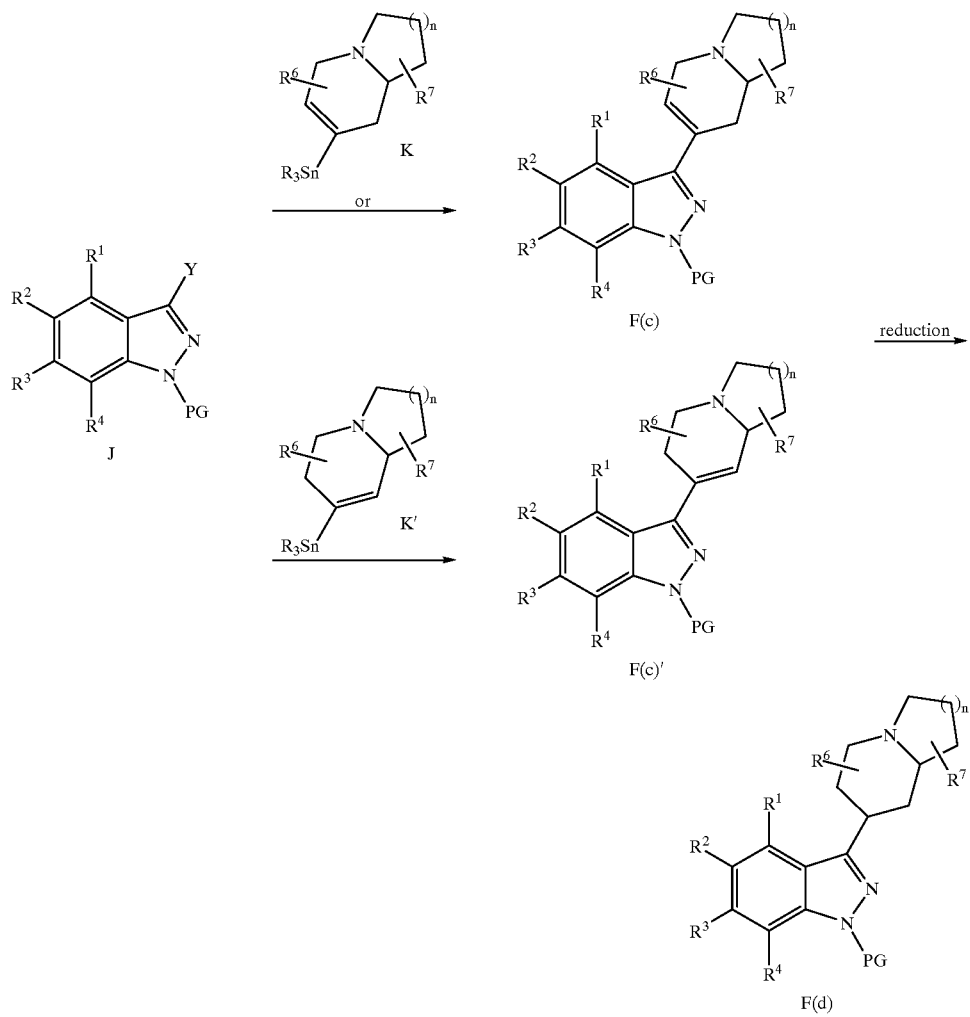

Compounds of Formula F, wherein $R^1$–$R^4$, $R^6$, $R^7$ and n are as defined in Formula I, X is $CR^{17}$, wherein $R^{17}$ is as defined in Formula I, Z is N and ——— is a single bond (Formula F(e)), may be prepared a compound of Formula M or a compound of Formula N, wherein $R^1$–$R^4$ are as defined in Formula I and PG is a suitable protecting group such as acetate or tosyl, may be reacted with a bicylic piperazine of Formula O, wherein $R^6$, $R^7$ and n are as defined in Formula I, in the presence of a catalytic amount of an acid, such as p-toluenesulfonic acid or camphorsulfonic acid, in an inert solvent such as toluene or benzene, at temperatures in the range of 25–120° C., to provide compounds of Formula F(e), wherein $R^1$–$R^4$, $R^6$, $R^7$ and n are as defined in Formula I and PG is a suitable protecting group. Preferred conditions are p-toluenesulfonic acid in toluene at a refluxing temperature.

Scheme 6

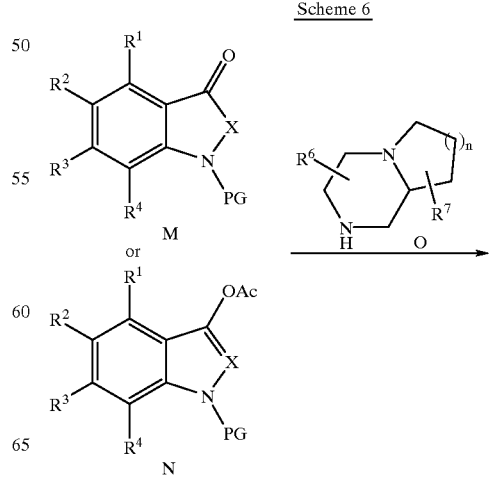

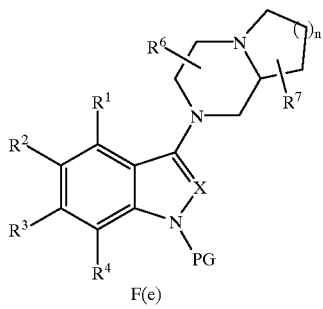

F(e)

Compounds of Formula F, wherein $R^1$–$R^4$, $R^6$, $R^7$ and n are as defined in Formula I, Z and X are both N and ——— is a single bond (Formula F(f)), may be prepared as shown in Scheme 7. Compounds of Formula J, wherein $R^1$–$R^4$ are as defined in Formula I, Y is a suitable leaving group such as halo, preferably chloro, and PG is an appropriate protecting group such as acetate or tosyl, preferably tosyl, may be reacted with a compound of Formula O, wherein $R^6$, $R^7$ and n are as defined in Formula I, either neat or in an inert solvent at temperatures in the range of 25–150° C. The reaction is preferably conducted neat at a temperature in the range of 100–130° C.

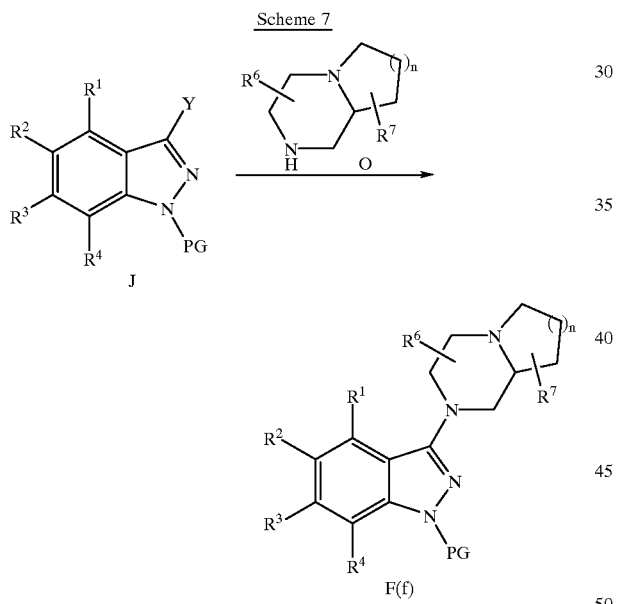

Scheme 7

Compounds of Formula I, wherein X is $CR^{17}$, wherein $R^{17}$ is selected from $C_{1-6}$alkyl and benzyl, may be prepared by treating compounds of Formula I or Formula F, wherein X is $CR^{17}$ and $R^{16}$ is H, with a strong base, such as n-butyllithium, in an inert solvent, such as tetrahydrofuran, at a temperature in the range of –100–0° C. (preferably –78° C.), followed by the addition of a reagent of formula $R^{17}$—Y, wherein $R^{17}$ is selected from $C_{1-4}$alkyl and benzyl and Y is a suitable leaving group such as bromo, followed by warming to room temperature.

Compounds of Formula G, wherein $R^1$–$R^4$ are as defined in Formula I and X is $CR^{17}$, wherein $R^{17}$ is as defined in Formula I, are either commercially available or can be prepared using standard procedures. For example, compounds of Formula G may be prepared using the well known Fischer indolization method (see March, J, Advanced Organic Chemistry, John Wiley & Sons, 1985, p. 1032–1033, and references found therein) or using the procedure shown in Scheme 8. 4-Substituted anilines of Formula P, wherein $R^1$–$R^4$ are as defined in Formula I, can be treated with reagents of Formula Q, wherein X is $CR^{17}$ and $R^{17}$ is as defined in Formula I, in the presence of a base such as sodium bicarbonate or potassium carbonate in an alcoholic solvent at temperatures in the range of 60–100° C., to provide intermediates of Formula S. Preferred conditions are sodium bicarbonate in ethanol at around 80° C. Intermediates of Formula S can be cyclized in the presence of reagents of Formula T, wherein R is, for example, methyl or trifluoromethyl (which is preferred) at temperatures in the range of 60–100° C., to provide indoles of Formula U. The preferred conditions are trifluoroacetic anhydride and trifluoroacetic acid at refluxing temperatures. Finally, compounds of Formula U can be treated under standard deprotection conditions, for example alkali hydroxides in an alcoholic solvent, to provide indoles of Formula G, wherein $R^1$–$R^4$ are as defined in Formula I and X is $CR^{17}$ wherein $R^{17}$ is as defined in Formula I. Preferred conditions for this reaction are potassium hydroxide in ethanol at room temperature. The reagents of Formula P and Q, are either commercially available or can be prepared using processes analogous to those established in the art.

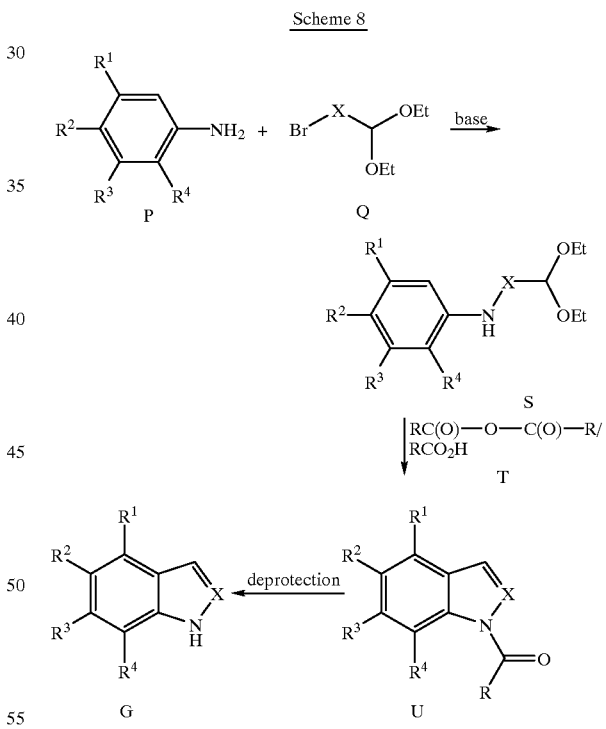

Scheme 8

Compounds of Formula J, wherein $R^1$–$R^4$ are as defined in Formula I, Y is a suitable leaving group and PG is a suitable protecting group can be prepared from the corresponding unprotected compound V using standard protecting group procedures as shown below in Scheme 9. For example, the introduction of the tosyl group is conveniently performed using tosyl chloride in the presence of a base such as tiethylamine in an inert solvent such as methylene chloride at temperatures in the range of 0–60° C., preferably room temperature.

Scheme 9

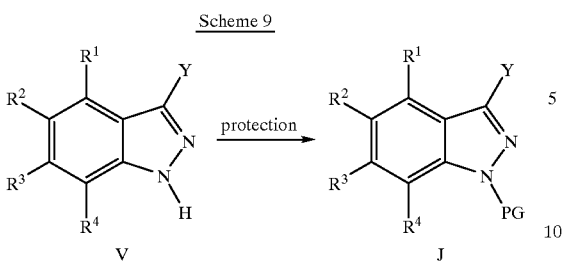

Compounds of Formula V wherein $R^1$–$R^4$ are as defined in Formula I and Y is a suitable leaving group are either commercially available or can be prepared using standard indazole synthesis procedures as described in *Organic Synthesis,* ed. Horning, E. C. John Wiley & Sons, 1955, vol. 3, p. 475–479; or Baker, R. et al. EP 494,774.

An alternative procedure for the preparation of compounds of Formula I, wherein X is N, is shown in Scheme 10 and is analogous to the procedure described in detail in Baker, R. et al. EP 494,774. Compounds of Formula W, wherein $R^1$–$R^4$, $R^6$, $R^7$, n, ——— and Z are as defined in Formula I and D is a readily displaceable group, such as a $C_{1-4}$alkanoyloxy group (suitably acetoxy) or an arylsulfoxy group (suitably tosyl), can be cyclized in a suitable organic solvent at an elevated temperature, for example a mixture of xylene and 2,6-lutidine at around 140° C., or in a melt, which requires a temperature of around 170° C., to provide compounds of Formula X, wherein $R^1$–$R^4$, $R^6$, $R^7$, n, ——— and Z are as defined in Formula I. The compounds of Formula I are thus available from compounds of Formula X by reaction with either a reagent of Formula B, C, D or E using the procedures decribed previously.

Scheme 10

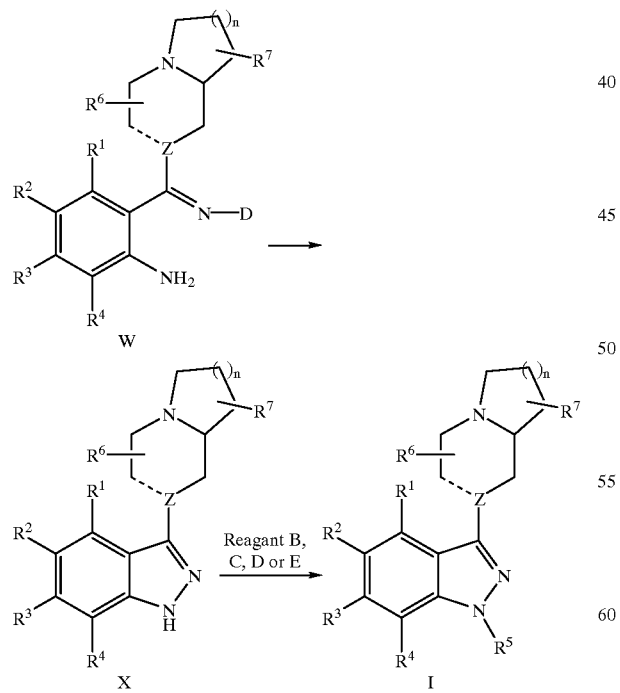

When D is acetoxy, compounds of Formula W, wherein $R^1$–$R^4$, $R^6$, $R^7$, n, ——— and Z are as defined in Formula I, may be prepared by treating the corresponding carbonyl compounds of Formula Y, wherein $R^1$–$R^4$, $R^6$, $R^7$, n, ——— and Z are as defined in Formula I, or a protected derivative thereof, with hydroxylamine hydrochloride, advantageously in pyridine at a refluxing temperature, followed by acylation with acetic anhydride, suitably in the presence of 4-dimethyaminopyridine in methylene chloride at room temperature, as shown in Scheme 11.

Scheme 11

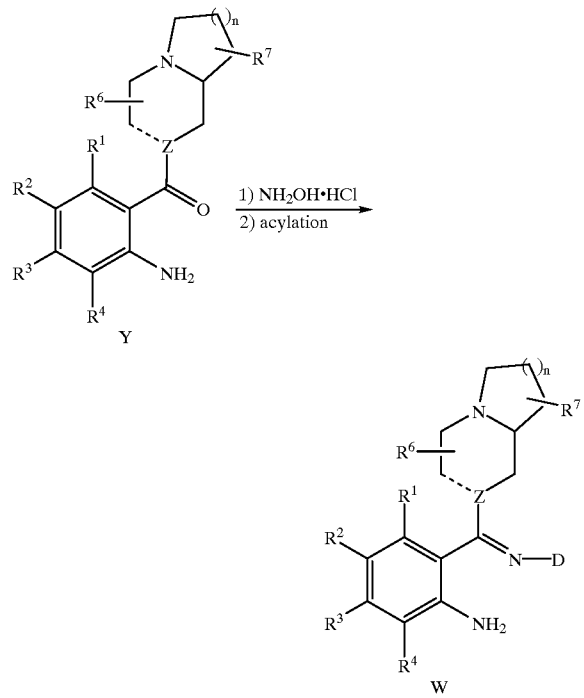

As shown in Scheme 12, the N-formyl protected derivative of compounds of Formula Y, wherein $R^1$–$R^4$, $R^6$, $R^7$, n, Z and ——— are as defined in Formula I, may be prepared by oxonolysis of an indole of Formula AA, wherein $R^1$–$R^4$, $R^6$, $R^7$, n, Z and ——— are as defined in Formula I and X is CH, (available from, for example, compounds of Formula F, wherein $R^1$–$R^4$, $R^6$, $R^7$, n, Z and ——— are as defined in Formula I and X is CH, by removal of the protecting group) followed by reductive workup, preferably using dimethylsulfide.

Scheme 12

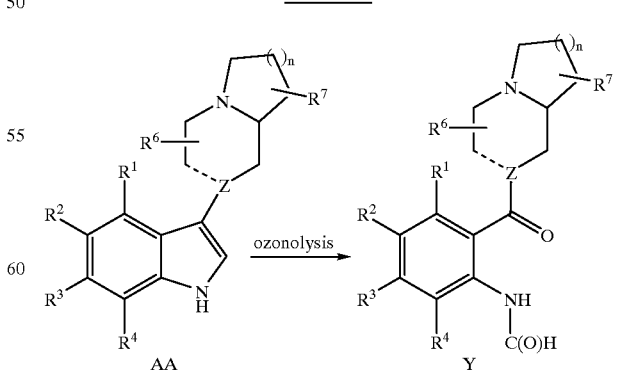

The bicyclic piperidinones H and piperizines O, wherein $R^6$, $R^7$ and n are as defined in Formula I, are either commercially available or can be prepared using procedures known in the art. For example, bicyclic piperidinones of Formula H may be prepared according to procedures described in King, F. D., J. Chem. Soc. Perkin Trans. 1, 1986:447–453 and bicyclic piperazines of Formula O may be prepared according to procedures described in Power, P. et al., U.S. Pat. No. 5,576,314; Saleh, M. A. et al. J. Org. Chem. 58, 1993:690–695; Urban, F. J. Heterocyclic Chem. 32, 1995:857–861; Bright, G. et al. WO 90/08148; de Costa, B. R. et al. J. Med. Chem. 36, 1993:2311–2320; and Botre, C. et al. J. Med. Chem. 29, 1986:1814–1820. The bicyclic piperidine K may be prepared from piperidinone H using standard chemistries, for example, by reacting the ketone with a base, such as lithium diisopropylamide or triethylamine, and a suitable triflating agent, such as N-phenyltriflimide or triflic anhydride, and converting the resulting triflate to a compound of Formula K by treatment with, for example, a palladium catalyst and a bis(trialkyltin). Alternatively, bicyclic piperidine K may be prepared by forming the tosylhydrazone of a compound of Formula H and using standard Shapiro conditions, trap the vinyl anion with a suitable reagent like tributyltin chloride.

It should be noted that one skilled in the art would realize that the sequence of reactions described above for the preparation of compounds of Formula I can be varied. For example, the $R^5$ group may be incorporated into the molecule before the addition of the group at the indole or indazole 3-position. Further, a compound of Formula I may be converted to another compound of Formula I using known chemistries, for example alkylation, arylation, oxidation/reduction and acylation to obtain the desired substitution at $R^1$ to $R^4$.

In some cases, the chemistries outlined above may have to be modified, for instance by use of protecting groups, to prevent side reactions due to reactive groups, such as reactive groups attached as substituents. This may be achieved be means of conventional protecting groups, as described in *Protective Groups in Organic Chemistry*, ed. McOmie, J. F. W. Plenum Press, 1973; and Greene, T. W. & Wuts, P.G.M., *Protective Groups in Organic Synthesis*, John Wiley & Sons, 1991.

In another of its aspects, the present invention provides compounds, useful as intermediates in the preparation of compounds of Formula I and having the general Formula II:

II

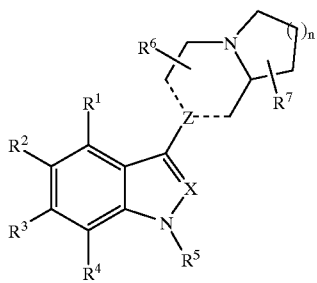

wherein $R^5$ is H and $R^1$–$R^4$, $R^6$–$R^{17}$, X, Z, n and ——— are as defined in Formula I (and a salt, solvate or hydrate thereof) and where embodiments of the Formula II compounds are as described above for Formula I compounds (excepting $R^5$).

Specific compounds of Formula II include:

5-Fluoro-3-[(8a-R,S)-1,2,3,5,8,8a-hexahydro-7-indolizinyl]-1H-indole;

3-[(6-R,S)-1,4-Diaza[4.3.0]bicyclonon-4-yl]-1H-indole;
3-[(6-R,S)-1,4-Diaza[4.4.0]bicyclodecan-4-yl]-1H-indole;
5-Methoxy-3-[(8a-R,S)-1,2,3,5,8,8a-hexahydro-7-indolizinyl]-1H-indole;
5-Methyl-3-[(8a-R,S)-1,2,3,5,8,8a-hexahydro-7-indolizinyl]-1H-indole;
7-Methyl-3-[(8a-R,S)-1,2,3,5,8,8a-hexahydro-7-indolizinyl]-1H-indole;
5,7-Difluoro-3-[(8a-R,S)-1,2,3,5,8,8a-hexahydro-7-indolizinyl]-1H-indole;
5-Fluoro-3-[(7-R,S)(8a-R,S)-octahydro-7-indolizinyl)-1H-indole;
5-Fluoro-3-[(7R or 7S)(8a-R,S)-octahydro-7-indolizinyl]-1H-indole, Isomer I;
5-Fluoro-3-[(7R or 7S)(8aR,S)-octahydro-7-indolizinyl]-1H-indole, Isomer II;
5-Methoxy-3-[(7R or 7S)(8a-R,S)-octahydro-7-indolizinyl]-1H-indole, Isomer I;
5-Methoxy-3-[(7R or 7S)(8a-R,S)-octahydro-7-indolizinyl]-1H-indole, Isomer II;
5,7-Difluoro-3-[(7R or 7S)(8a-R,S)-octahydro-7-indolizinyl]-1H-indole, Isomer I; and
5,7-Difluoro-3-[(7R or 7S)(8a-R,S)-octahydro-7-indolizinyl]-1H-indole, Isomer II.

In a further aspect of the present invention, compounds of Formula I, specifically compounds of Formula I wherein $R^5$ is selected from $CH_2Ar$, $SO_2Ar$ and $C(O)Ar$, are useful as intermediates in the preparation of compounds of Formula II, which may be used as antimigraine agents as described in a co-pending application filed on an even date herewith and the contents of which are incorporated herein by reference.

In another embodiment of the invention, compounds of Formula I can be used to distinguish 5-$HT_6$ receptors from other receptor subtypes, for example glutamate or opioid receptors, within a population of receptors, and in particular to distinguish between the 5-$HT_6$ and other 5-HT receptor subtypes. The latter can be achieved by incubating preparations of the 5-$HT_6$ receptor and one of the other 5-HT receptor subtypes (for example 5-$HT_{2A}$) with a 5-$HT_6$-selective compound of the invention and then incubating the resulting preparation with a radiolabeled serotonin receptor ligand, for example [$^3$H]-serotonin. The 5-$HT_6$ receptors are then distinguished by determining the difference in membrane-bound activity, with the 5-$HT_6$ receptor exhibiting lesser radioactivity, i.e., lesser [$^3$H]-serotonin binding, than the other 5-HT receptor subtype.

In another embodiment of the invention, a compound of Formula I is provided in labeled form, such as radiolabeled form, e. g. labeled by incorporation within its structure $^3$H or $^{14}$C or by conjugation to $^{125}$I. In another aspect of the invention, the compounds in labeled form can be used to identify 5-$HT_6$ receptor ligands by techniques common in the art. This can be achieved by incubating the receptor or tissue in the presence of a ligand candidate and then incubating the resulting preparation with an equimolar amount of radiolabeled compound of the invention such as [$I^{123}$]-1-(4-iodophenylsulfonyl)-5-fluoro-3-[(8a-R,S)-1,2,3,5,8,8a-hexahydro-7-indolizinyl]indole. 5-$HT_6$ receptor ligands are thus revealed as those that are not significantly displaced by the radiolabeled compound of the present invention. Alternatively, 5-$HT_6$ receptor ligand candidates may be identified by first incubating a radiolabeled form of a compound of the invention then incubating the resulting preparation in the presence of the candidate ligand. A more potent 5-$HT_6$ receptor ligand will, at equimolar concentration, displace the radiolabeled compound of the invention.

A radiolabelled compound of Formula I may be prepared using standard methods known in the art. For example a compound of Formula I wherein one of $R^1$–$R^4$ is radioactive iodo or Ar is substituted with a radioactive iodo group may be prepared from the corresponding tialkyltin (suitably timethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis (triphenylphosphine) palladium (0) in an inert solvent, such as dioxane, and at elevated temperatures, suitably 50–100° C. Alternatively, tritium may be incorporated into a compound of Formula I using standard techniques, for example by hydrogenation of a suitable precursor to a compound of Formula I using tritium gas and a catalyst.

Compounds of Formula I are useful as pharmaceuticals for the treatment of various conditions in which the use of a 5-$HT_6$ antagonist is indicated, such as psychosis, schizophrenia, manic depression, depression, neurological disturbances, memory disturbances, Parkinsonism, amylotrophic lateral sclerosis, Alzheimer's disease and Huntington's disease. In another of its aspects, the present invention provides pharmaceutical compositions useful to treat 5-$HT_6$-related medical conditions, in which a compound of Formula I is present in an amount effective to antagonize 5-$HT_6$ receptor stimulation, together with a pharmaceutically acceptable carrier. In a related aspect, the invention provides a method for treating medical conditions for which a 5-$HT_6$ receptor antagonist is indicated, which comprises the step of administering to the patient an amount of a compound of Formula I effective to antagonize 5-$HT_6$ receptor stimulation, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit dosages, i.e. therapeutically effective amounts, can be determined during clinical trials designed appropriately for each of the conditions for which administration of a chosen compound is indicated and will of course vary depending on the desired clinical endpoint. Each dosage unit for oral administration may contain from 0.01 to 500 mg/kg (and for parenteral administration may contain from 0.1 to 50 mg) of a compound of Formula I, or a pharmaceutically acceptable salt thereof calculated as the free base, and will be administered in a frequency appropriate for initial and maintenance treatments. For laboratory use, the present compounds can be stored in packaged form for reconstitution and use.

EXPERIMENTAL EXAMPLES

EXAMPLE 1

(a): 1-Acetyl-3-[(6-R,S)-1,4-diaza[4.3.0]bicyclonon-4-yl]indole

A solution of 1-acetoxy-3-indolone (300 mg, 1.88 mmol), 1,4-diaza[4.3.0]bicyclononane (475 mg, 3.77 mmol) and p-toluenesulfonic acid (20 mg) in dry toluene (15 mL) was refluxed through a Dean-Stark trap for 24 hours. The mixture was diluted with methylene chloride, filtered through silica gel and purified by silica gel chromatography (7.5% methanol in methylene chloride) to give the title compound as a brown oil (140 mg, 26%); $^1$H NMR (CDCl$_3$) δ: 8.46 (br s,1H), 7.57 (d, 1H), 7.33 (t, 1H), 7.25 (t, 1H), 6.79 (br s, 1H), 5.65 (m, 1H), 3.52 (m, 1H), 3.13 (m, 2H), 2.85 (m, 1H), 2.57 (s, 3H), 2.53–1.44 (m, 8H); $^{13}$C NMR (CDCl$_3$) δ: 168.1, 136.9, 135.5, 126.2, 125.5, 123.1, 119.3, 117.0, 109.4, 62.3, 56.4, 53.5, 51.2, 27.5, 24.2, 21.3;

In a like manner, the following additional compound was prepared:

(b) 1-Acetyl-3-[(6-R,S)-1,4-diaza[4.4.0]bicyclodecan-4-yl]indole: from 1,4-diaza[4.4.0]bicyclodecane, 27%, brown oil; $^1$H NMR (CDCl$_3$) δ: 8.44 (br s, 1H), 7.54 (d, 1H), 7.32 (t, 1H), 7.23 (t, 1H), 6.74 (br s, 1H), 3.48 (m, 1H), 3.32 (m, 1H), 2.80–2.82 (m, 4H), 2.55 (s, 3H), 2.53–1.20 (m, 9H); $^{13}$C NMR (CDCl$_3$) δ: 168.1, 136.7, 135.5, 125.5, 123.1, 119.3, 116.9, 109.2, 60.9, 57.7, 55.6, 54.8, 51.7, 29.7, 25.6, 24.2, 23.9;

EXAMPLE 2

(a): 3-[(6-R,S)-1,4-Diaza[4.3.0]bicyclonon-4-yl]-1H-indole

To a solution of 1-acetyl-3-[(6-R,S)-1,4-diaza[4.3.0]bicyclonon-4-yl]-1H-indole (Example 1a, 122 mg, 0.43mmol), in methanol (10 mL) was added sodium hydroxide (26 mg, 0.65 mmol) and the resulting solution was refluxed for 15 minutes. The reaction mixture was then poured into ethyl acetate, washed with water and brine and the organic layer dried (Na$_2$SO$_4$), filtered and concentrated to give the title compounds as yellow oil (102 mg, 100%); $^1$H NMR (CDCl$_3$) δ: 8.01, (br s, 1H), 7.65 (d, 1H), 7.28 (d, 7H), 7.17 (t, 1H), 7.07 (t, 1H), 6.72 (d, 1H), 3.65 (m,1H), 3.50 (m, 1H), 2.90 (m, 4H), 2.65–1.25 (m, 9H); $^{13}$C NMR (CDCl$_3$) δ: 135.7, 132.2, 122.2, 119.1, 118.8, 111.4, 110.6, 62.7, 57.4, 53.5, 52.0, 51.8, 27.5, 21.3;

In a like manner, the following additional compound was prepared:

(b) 3-[(6-R,S)-1,4-Diaza[4.4.0]bicyclodecan-4-yl]-1H-indole: from 1-acetyl-3-[(6-R,S)-1,4-diaza[4.4.0]bicyclodecan-4-yl]-1H-indole (Example 1b), 88%, yellow oil; $^1$H NMR (CDCl$_3$) δ: 7.89 (br s ,1H), 7.64(d, 1H), 7.27 (d, 1H), 7.17 (t, 1H), 7.07 (t, 1H), 6.70 (d, 1H), 3.47 (m, 1H), 3.36 (m,1H), 2.90 (m, 4H) 2.65–1.24 (m, 9H); $^{13}$C NMR (CDCl$_3$), δ: 135.7, 132.3, 122.1, 119.1, 118.8, 111.4, 110.3, 61.3, 58.8, 55.6, 55.2, 52.6, 29.8, 25.7, 24.0;

EXAMPLE 3

3-Chloro-1-(4-methylphenylsulfonyl)indazole p-toluenesulfonyl chloride (750 mg, 3.93 mmol) in methylene chloride was added triethylamine (1.4 mL, 9.83 mmol) and the resulting solution was stirred at room temperature overnight. The reaction was concentrated and purified by silica gel chromatography (20% ethyl acetate in hexanes) to provide the title compound as a white solid (890 mg, 89%).

EXAMPLE 4

(a): 5-Fluoro-3-[(8a-R,S)-1,2,3,5,8,8a-hexahydro-7-indolizinyl]-1H-indole

5-Fluoro-1H-indole (1.0 g, 7.4 mmoles), octahydroindolizin-7-one (King, F. D., J. Chem. Soc. Perkin Trans. I, 1986:447–453, 1.03 g, 7.4 mmoles) and pyrrolidine (6.6 mL, 74 mmoles) were mixed in ethanol (10 mL) and refluxed for 72 hours. The resulting solid, collected by filtration, washed with methanol and dried to provide the title compound (1.48 g, 78 %).

In a like manner, the following additional compounds were prepared:

(b) 5-Methoxy-3-[(8a-R,S)-1,2,3,5,8,8a-hexahydro-7-indolizinyl]-1H-indole: from 5-methoxy-1H-indole, 63%.
(c) 5-Methyl-3-[(8a-R,S)-1,2,3,5,8,8a-hexahydro-7-indolizinyl]-1H-indole: from 5-methyl-1H-indole, 21%.
(d) 7-Methyl-3-[(8a-R,S)-1,2,3,5,8,8a-hexahydro-7-indolizinyl]-1H-indole: from 7-methyl-1H-indole, 24%.
(e) 5,7-Difluoro-3-[(8a-R,S)-1,2,3,5,8,8a-hexahydro-7-indolizinyl]-1 H-indole: from 5,7-difluoro-1H-indole, 65%.

EXAMPLE 5

(a): 5-Fluoro-3-[(7-R or S)(8a-R,S)-octahydro-7-indolizinyl)-1H-indole (major diasteromer) and (b) 5-Fluoro-3-[(7-R or S)(8a-R,S)-octahydro-7-indolizinyl]-1H-indole (minor diastereomer)

5-Fluoro-3-[(8a-R,S)-1,2,3,5,8,8a-hexahydro-7-indolizinyl]-1H-indole (Example 4a, 500 mg, 1.95 mmol) and 10% Pd/C (250 mg) in ethanol (5 mL) were reacted under an atmosphere of H$_2$ at room temperature overnight. The resulting solution was filtered and purified using silica gel chromatography. Two diastereomers were obtained. The major diastereomer (300 mg, 59%) was eluted with 2% ammonia/methanol in dichloromethane, and the minor diastereomer (88 mg, 17%), eluted with with 10% ammonia/methanol in dichloromethane.

EXAMPLE 6

(a): 3-[(6-R,S)-1,4-Diaza[4.3.0]bicyclonon-4-yl]-1-(2-naphthalenesulfonyl)indole To a solution of 3-[(6-R,S)-1,4-diaza[4.3.0]bicyclonon-4-yl]-1H-indole (Example 2a, 3 mg, 0.012 mmol) in THF (5 mL) cooled to 0° C. under argon, was added sodium bis(trimethylsilyl)amide (1M solution in THF, 40 μL, 0.040 mmol) and the resulting solution was stirred for 5 minutes. 2-Naphthalenesulfonyl chloride (5 mg, 0.022 mmol) was then added and the solution stirred for 2 hours. Silica gel (2 g) and 2 drops water were then added to quench the reaction and the resulting slurry was applied to a silica gel column. Elution with 5% methanol in dichloromethane provided the title compound as a yellow oil.

In a like manner, the following additional compounds were prepared:

(b) 3-[(6-R,S)-1,4-Diaza[4.3.0]bicyclonon-4-yl]-1-(1-naphthalenesulfonyl)indole: from 1-naphthalenesulfonyl chloride and 3-[(6-R,S)-1,4-diaza[4.3.0]bicyclonon-4-yl]-1H-indole (Example 2a), yellow oil;
(c) 1-(4-Bromophenylsulfonyl)-3-[(6-R,S)-1,4-diaza[4.3.0]bicyclonon-4-yl]indole: from 4-bromophenylsulfonyl chloride and 3-[(6-R,S)-1,4-diaza[4.3.0]bicyclonon-4-yl]-1H-indole (Example 2a), yellow oil;
(d) 1-(4-t-Butylphenylsulfonyl)-3-[(6-R,S)-1,4-diaza[4.3.0]bicyclonon-4-yl]indole: from 4-t-butylphenylsulfonyl chloride and 3-[(6-R,S)-1,4-diaza[4.3.0]bicyclonon-4-yl]-1H-indole (Example 2a), yellow oil;
(e) 1-(4-Chlorophenylsulfonyl)-3-[(6-R,S)-1,4-diaza[4.3.0]bicyclonon-4-yl]indole: from 4-chlorophenylsulfonyl chloride and 3-[(6-R,S)-1,4-diaza[4.3.0]bicyclonon-4-yl]-1H-indole (Example 2a), yellow oil;
(f) 3-[(6-R,S)-1,4-Diaza[4.3.0]bicyclonon-4-yl]-1-(4-fluorophenylsulfonyl)indole: from 4-fluorophenylsulfonyl chloride and 3-[(6-R,S)-1,4-diaza[4.3.0]bicyclonon-4-yl]-1H-indole (Example 2a), yellow oil;
(g) 3-[(6-R,S)-1,4-Diaza[4.3.0]bicyclonon-4-yl]-1-(4-methoxyphenylsulfonyl)indole: from 4-methoxyphenylsulfonyl chloride and 3-[(6-R,S)-1,4-diaza[4.3.0]bicyclonon-4-yl]-1H-indole (Example 2a), yellow oil;
(h) 3-[(6-R,S)-1,4-Diaza[4.3.0]bicyclonon-4-yl]-1-(2,5-dichlorophenylsulfonyl)indole: from 2,5-dichlorophenylsulfonyl chloride and 3-[(6-R,S)-1,4-diaza[4.3.0]bicyclonon-4-yl]-1H-indole (Example 2a), yellow oil;

(i) 1-(2-Bromophenylsulfonyl)-3-[(6-R,S)-1,4-diaza[4.3.0]bicyclonon-4-yl]indole: from 2-bromophenylsulfonyl chloride and 3-[(6-R,S)-1,4-diaza[4.3.0]bicyclonon-4-yl]-1H-indole (Example 2a), yellow oil;

(j) 3-[(6-R,S)-1,4-Diaza[4.3.0]bicyclonon-4-yl]-1-(phenylsulfonyl)indole: from phenylsulfonyl chloride and 3-[(6-R,S)-1,4-diaza[4.3.0]bicyclonon-4-yl]-1H-indole (Example 2a), yellow oil;

(k) 3-[(6-R,S)-1,4-Diaza[4.3.0]bicyclonon-4-yl]-1-(4-methylphenylsulfonyl)indole: from 4-methylphenylsulfonyl chloride and 3-[(6-R,S)-1,4-diaza[4.3.0]bicyclonon-4-yl]-1H-indole (Example 2a), yellow oil;

(l) 3-[(6-R,S)-1,4-Diaza[4.4.0]bicyclodecan-4-yl]-1-(2-naphthalenesulfonyl)indole: from 2-naphthalenesulfonyl chloride and 3-[(6-R,S)-1,4-diaza[4.4.0]bicyclodecan-4-yl]-1H-indole (Example 2b), yellow oil;

(m) 3-[(6-R,S)-1,4-Diaza[4.4.0]bicyclodecan-4-yl]-1-(1-naphthalenesulfonyl)indole: from 1-naphthalenesulfonyl chloride and 3-[(6-R,S)-1,4-diaza[4.4.0]bicyclodecan-4-yl]-1H-indole (Example 2b), yellow oil;

(n) 1-(4-Bromophenylsulfonyl)-3-[(6-R,S)-1,4-diaza[4.4.0]bicyclodecan-4-yl]indole: from 4-bromophenylsulfonyl chloride and 3-[(6-R,S)-1,4-diaza[4.4.0]bicyclodecan-4-yl]-1H-indole (Example 2b), yellow oil;

(o) 1-(4-t-Butylphenylsulfonyl)-3-[(6-R,S)-1,4-diaza[4.4.0]bicyclodecan-4-yl]indole: from 4-t-butylphenylsulfonyl chloride and 3-[(6-R,S)-1,4-diaza[4.4.0]bicyclodecan-4-yl]-1H-indole (Example 2b), yellow oil;

(p) 1-(4-Chlorophenylsulfonyl)-3-[(6-R,S)-1,4-diaza[4.4.0]bicyclodecan-4-yl]indole: from 4-chlorophenylsulfonyl chloride and 3-[(6-R,S)-1,4-diaza[4.4.0]bicyclodecan-4-yl]-1H-indole (Example 2b), yellow oil;

(q) 3-[(6-R,S)-1,4-Diaza[4.4.0]bicyclodecan-4-yl]-1-(4-fluorophenylsulfonyl)indole: from 4-fluorophenylsulfonyl chloride and 3-[(6-R,S)-1,4-diaza[4.4.0]bicyclodecan-4-yl]-1H-indole (Example 2b), yellow oil;

(r) 3-[(6-R,S)-1,4-Diaza[4.4.0]bicyclodecan-4-yl]-1-(4-methoxyphenylsulfonyl)indole: from 4-methoxyphenylsulfonyl chloride and 3-[(6-R,S)-1,4-diaza[4.4.0]bicyclodecan-4-yl]-1H-indole (Example 2b), yellow oil;

(s) 3-[(6-R,S)-1,4-Diaza[4.4.0]bicyclodecan-4-yl]-1-(2,5-dichlorophenylsulfonyl)indole: from 2,5-dichlorophenylsulfonyl chloride and 3-[(6-R,S)-1,4-diaza[4.4.0]bicyclodecan-4-yl]-1H-indole (Example 2b), yellow oil;

(t) 1-(2-Bromophenylsulfonyl)-3-[(6-R,S)-1,4-diaza[4.4.0]bicyclodecan-4-yl]indole: from 2-bromophenylsulfonyl chloride and 3-[(6-R,S)-1,4-diaza[4.4.0]bicyclodecan-4-yl]-1H-indole (Example 2b), yellow oil;

(u) 3-[(6-R,S)-1,4-Diaza[4.4.0]bicyclodecan-4-yl]-1-(phenylsulfonyl)indole: from phenylsulfonyl chloride and 3-[(6-R,S)-1,4-diaza[4.4.0]bicyclodecan-4-yl]-1H-indole (Example 2b), yellow oil;

(v) 3-[(6-R,S)-1,4-Diaza[4.4.0]bicyclodecan-4-yl]-1-(4-methylphenylsulfonyl)indole: from 4-methylphenylsulfonyl chloride and 3-[(6-R,S)-1,4-diaza[4.4.0]bicyclodecan-4-yl]-1H-indole (Example 2b), yellow oil;

(w) 3-[(6-R,S)-1,4-Diaza[4.4.0]bicyclodecan-4-yl]-1-(2,4,6-trimethylphenylsulfonyl)indole: from 2,4,6-trimethylphenylsulfonyl chloride and 3-[(6-R,S)-1,4-diaza[4.4.0]bicyclodecan-4-yl]-1H-indole (Example 2b), yellow oil;

(x) 5-Fluoro-3-[(8a-R,S)-1,2,3,5,8,8a-hexahydro-7-indolizinyl]-1-phenylsulfonylindole: from 5-fluoro-3-[(8a-R,S)-1,2,3,5,8,8a-hexahydro-7-indolizinyl]-1H-indole (Example 4a) and benzenesulfonyl chloride, 48.2%; HRMS-FAB MH$^+$ for $C_{22}H_{21}N_2FO_2S$: calc'd 397.1386, found 397.14242.

(y) 5-Fluoro-3-[(8a-R,S)-1,2,3,5,8,8a-hexahydro-7-indolizinyl]-1-(1-naphthalenesulfonyl)indole: from 5-fluoro-3-[(8a-R,S)-1,2,3,5,8,8a-hexahydro-7-indolizinyl]-1H-indole (Example 4a) and 1-naphthalenesulfonyl chloride, 56.6%; HRMS-FAB MH$^+$ for $C_{26}H_{23}N_2FO_2S$: calc'd 447.15425, found 447.15366.

(z) 5-Fluoro-3-[(8a-R,S)-1,2,3,5,8,8a-hexahydro-7-indolizinyl]-1-(2-naphthalenesulfonyl)indole: from 5-fluoro-3-[(8a-R,S)-1,2,3,5,8,8a-hexahydro-7-indolizinyl]-1H-indole (Example 4a) and 2-naphthalenesulfonyl chloride, 33%; HRMS-FAB MH$^+$ for $C_{26}H_{23}N_2FO_2S$:, calc'd 447.15425, found 447.15054.

(aa) 5-Fluoro-1-(4-fluorophenylsulfonyl)-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 4-fluorobenzenesulfonyl chloride, 97%; HRMS-FAB MH$^+$ for $C_{22}H_{20}N_2F_2O_2S$: calc'd 415.12918, found 415.13216.

(bb) 1-(4-Bromophenylsulfonyl)-5-fluoro-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 4-bromobenzenesulfonyl chloride, 35%; HRMS-FAB MH$^+$ for $C_{22}H_{20}N_2BrFO_2S$: calc'd 475.0491 1, found 475.04536.

(cc) 1-(2-Bromophenylsulfonyl)-5-fluoro-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 2-bromobenzenesulfonyl chloride, 85%; HRMS-FAB MH$^+$ for $C_{22}H_{20}N_2BrFO_2S$: calc'd 475.04911, found 475.04807.

(dd) 5-Fluoro-3-[(8a-R,S)-1,2,3,5,8,8a-hexahydro-7-indolizinyl]-1-(4-methylphenylsulfonyl)indole: from 5-fluoro-3-[(8a-R,S)-1,2,3,5,8,8a-hexahydro-7-indolizinyl]-1H-indole (Example 4a) and p-toluenesulfonyl chloride, 96%; HRMS-FAB MH$^+$ for $C_{23}H_{23}N_2FO_2S$: calc'd 411.15425, found 411.1568.

(ee) 5-Fluoro-3-[(8a-R,S)-1,2,3,5,8,8a-hexahydro-7-indolizinyl]-1-(4-methoxyphenylsulfonyl)indole: from 5-fluoro-3-[(8a-R,S)-1,2,3,5,8,8a-hexahydro-7-indolizinyl]-1H-indole (Example 4a) and 4-methoxybenzenesulfonyl chloride, 57%; HRMS-FAB MH$^+$ for $C_{23}H_{23}N_2FO_3S$: calc'd 427.14916, found 427.14701.

(ff) 5-Fluoro-3-[(8a-R,S)-1,2,3,5,8,8a-hexahydro-7-indolizinyl]-1-(2,4,6-trimethylphenylsulfonyl)indole: from 5-fluoro-3-[(8a-R,S)-1,2,3,5,8,8a-hexahydro-7-indolizinyl]-1H-indole (Example 4a) and 2,4,6-trimethylbenzenesulfonyl chloride, 47%; HRMS-FAB MH$^+$ for $C_{25}H_{27}N_2FO_2S$: calc'd 439.18555, found 439.18681.

(gg) 1-(4-t-Butylphenylsulfonyl)-5-fluoro-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 4-tert-butylphenylsulfonyl chloride, 83%; HRMS-FAB MH$^+$ for $C_{26}H_{29}N_2FO_2S$: calc'd 453.20120, found 453.20313.

(hh) 1-(2,5-Dichlorophenylsulfonyl)-5-fluoro-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 2,5-dichlorophenylsulfonyl chloride, 72%; HRMS-FAB MH$^+$ for $C_{22}H_{19}N_2Cl_2FO_2S$: calc'd 465.06065, found 465.05986.

(ii) 1-(4-Chlorophenylsulfonyl)-5-fluoro-3-[(8a-R,S)-1,2,3,5,8,8a-hexahydro-7-indolizinyl]indole: from 5-fluoro-3-[(8a-R,S)-1,2,3,5,8,8a-hexahydro-7-indolizinyl]-1H-indole (Example 4a) and 4-chlorophenylsulfonyl chloride, 46.4%; HRMS-FAB MH+ for $C_{22}H_{19}N_2Cl_2FO_2S$: calc'd 431.099964, found 431.09809.

(jj) 5,7-Difluoro-3-[(8a-R,S)-1,2,3,5,8,8a-hexahydro-7-indolizinyl]-1-phenylsulfonylindole: from 5,7-fluoro-3-[(8a-R,S)-1,2,3,5,8,8a-hexahydro-7-indolizinyl]-1H-indole (Example 4e) and benzenesulfonyl chloride, 56%.

(kk) 5,7-Difluoro-3-[(8a-R,S)-1,2,3,5,8,8a-hexahydro-7-indolizinyl]-1-naphthalenesulfonylindole: from 5,7-fluoro-3-[(8a-R,S)-1,2,3,5,8,8a-hexahydro-7-indolizinyl]-1H-indole (Example 4e) and 1-naphthalenesulfonyl chloride, 45%.

(ll) 5,7-Difluoro-3-[(8a-R,S)-1,2,3,5,8,8a-hexahydro-7-indolizinyl]-2-naphthalenesulfonylindole: from 5,7-fluoro-3-[(8a-R,S)-1,2,3,5,8,8a-hexahydro-7-indolizinyl]-1H-indole (Example 4e) and 2-naphthalenesulfonyl chloride, 4%.

(mm) 5-Methoxy-3-[(8a-R,S)-1,2,3,5,8,8a-hexahydro-7-indolizinyl]-1-phenylsulfonylindole: from 5-methoxy-3-[(8a-R,S)-1,2,3,5,8,8a-hexahydro-7-indolizinyl]-1H-indole (Example 4b) and benzenesulfonyl chloride, 69%.

(nn) 5-Methoxy-3-[(8a-R,S)-1,2,3,5,8,8a-hexahydro-7-indolizinyl]-1-naphthalenesulfonylindole: from 5-methoxy-3-[(8a-R,S)-1,2,3,5,8,8a-hexahydro-7-indolizinyl]-1H-indole (Example 4b) and 1-naphthalenesulfonyl chloride, 61%.

(oo) 5-Methoxy-3-[(8a-R,S)-1,2,3,5,8,8a-hexahydro-7-indolizinyl]-2-naphthalenesulfonylindole: from 5-methoxy-3-[(8a-R,S)-1,2,3,5,8,8a-hexahydro-7-indolizinyl]-1H-indole (Example 4b) and 2-naphthalenesulfonyl chloride, 83%.

(pp) 5-Methyl-3-[(8a-R,S)-1,2,3,5,8,8a-hexahydro-7-indolizinyl]-1-phenylsulfonylindole: from 5-methyl-3-[(8a-R,S)-1,2,3,5,8,8a-hexahydro-7-indolizinyl]-1H-indole (Example 4c) and benzenesulfonyl chloride, 57%.

(qq) 5-Methyl-3-[(8a-R,S)-1,2,3,5,8,8a-hexahydro-7-indolizinyl]-1-naphthalenesulfonylindole: from 5-methyl-3-[(8a-R,S)-1,2,3,5,8,8a-hexahydro-7-indolizinyl]-1H-indole (Example 4c) and 1-naphthalenesulfonyl chloride, 56%.

(rr) 5-Methyl-3-[(8a-R,S)-1,2,3,5,8,8a-hexahydro-7-indolizinyl]-2-naphthalenesulfonylindole: from 5-methyl-3-[(8a-R,S)-1,2,3,5,8,8a-hexahydro-7-indolizinyl]-1H-indole (Example 4c) and 2-naphthalenesulfonyl chloride, 68%.

(ss) 7-Methyl-3-[(8a-R,S)-1,2,3,5,8,8a-hexahydro-7-indolizinyl]-1-phenylsulfonylindole: from 7-methyl-3-[(8a-R,S)-1,2,3,5,8,8a-hexahydro-7-indolizinyl]-1H-indole (Example 4d) and benzenesulfonyl chloride, 32%.

(tt) 7-Methyl-3-[(8a-R,S)-1,2,3,5,8,8a-hexahydro-7-indolizinyl]-1-naphthalenesulfonylindole: from 7-methyl-3-[(8a-R,S)-1,2,3,5,8,8a-hexahydro-7-indolizinyl]-1H-indole (Example 4d) and 1-naphthalenesulfonyl chloride, 26%.

(uu) 7-Methyl-3-[(8a-R,S)-1,2,3,5,8,8a-hexahydro-7-indolizinyl]-2-naphthalenesulfonylindole: from 7-methyl-3-[(8a-R,S)-1,2,3,5,8,8a-hexahydro-7-indolizinyl]-1H-indole (Example 4d) and 2-naphthalenesulfonyl chloride, 33%.

EXAMPLE 7

(a): 3-[(6-R,S)-1,4-Diaza[4.3.0]bicyclonon-4-yl]-1-(4-methylphenylsulfonyl)indazole 3-Chloro-1-(4-methylphenylsulfonyl)indazole (Example 3, 100 mg, 0.23 mmol) and 1,4-diaza[4.3.0]bicyclononane (1 mL) were mixed and stirred at 120° C. overnight. The reaction mixture was applied to a silica gel column and eluted with 5% methanol in methylene chloride to provide the title compound as a light yellow oil (129 mg, 31%).

In a like manner, the following addition compound was prepared:

(b) 3-[(6-R,S)-1,4-Diaza[4.4.0]bicyclodecan-4-yl]-1-(4-methylphenylsulfonyl)indazole: from 1,4-diaza[4.4.0]bicyclodecane, light yellow oil, 38%.

EXAMPLE 8

5-Fluoro-3-(1,2,3,5,8,8a-hexahydrohydro-7-indolizinyl)-1-(3-methylphenyl)indole

5-Fluoro-3-(1,2,3,5,8,8a-hexahydrohydro-7-indolizinyl)-1H-indole (Example 4a, 50 mg, 0.20 mmol) and 3-iodotoluene (65.4 mg, 0.30 mmol) were mixed with $K_2CO_3$ (41.4 mg, 0.30 mmol), CuBr (17.2 mg, 0.12 mmol) and Cu powder (7.8 mg, 0.12 mmol) in NMP (1 mL) and heated to 160~170° C. for 15 hr. The reaction was quenched by adding water and the resulting solid was collected by filtration. The solid was redissolved in dichloromethane, filtered through celite and the solid, evaporated. The product was purifed using silica gel chromatography (2% ammonia/methanol in dichloromethane) to provide the title compound (41 mg, 60.7%).

EXAMPLE 9

(a): 5-Fluoro-3-[(7-R,S)(8a-R,S)-octahydro-7-indolizinyl]-1-(3-methylphenyl)indole 5-Fluoro-3-[(8a-R,S)-1,2,3,5,8,8a-hexahydro-7-indolizinyl]-1-(3-methylphenyl)indole (Example 8, 35 mg, 0.10 mmol) and 10% Pd/C (50 mg) in ethanol (2 mL) were reacted under an atmosphere of $H_2$ at room temperature overnight. The resulting solution was filtered, evaporated and the product purified by silica gel chromatography using 2% 2M ammonia/methanol in dichloromethane as the eluent to provide the title compound (3.3 mg, 9.4%).

In a like manner, the following additional compounds were prepared:

(b) 5-Fluoro-3-[(7R or 7S)(8a-R,S)-octahydro-7-indolizinyl]-1H-indole, Isomer I (300 mg, 59%) and (c) 5-Fluoro-3-[(7R or 7S)(8aR,S)-octahydro-7-indolizinyl]-1H-indole, Isomer II (88 mg, 17%): from 5-fluoro-3-[(8a-R,S)-1,2,3,5,8,8a-hexahydro-7-indolizinyl]-1H-indole (Example 4a, 500 mg, 1.95 mmol) and 10% Pd/C (250 mg) in ethanol (5 mL) under $H_2$ at RT.

(c) 5-Methoxy-3-[(7R or 7S)(8a-R,S)-octahydro-7-indolizinyl]-1H-indole, Isomer I (152.7 mg, 58.7%) and (d) 5-Methoxy-3-[(7R or 7S)(8a-R,S)-octahydro-7-indolizinyl]-1H-indole, Isomer II ( 47.1 mg, 18.1%): from 5-methoxy-3-[(8a-R,S)-1,2,3,5,8,8a-hexahydro-7-indolizinyl]-1H-indole (Example 4b, 258.2 mg, 0.962 mmol) and 10% Pd/C (200 mg) in ethanol (3 mL) under $H_2$ at RT.

(e) 5,7-Difluoro-3-[(7R or 7S)(8a-R,S)-octahydro-7-indolizinyl]-1H-indole, Isomer I (94.7 mg, 33%) and (f) 5,7-Difluoro-3-[(7R or 7S)(8a-R,S)-octahydro-7-indolizinyl]-1H-indole, Isomer II (19.8 mg, 7%): from 5,7-difluoro-3-[(8a-R,S)-1,2,3,5,8,8a-hexahydro-7-indolizinyl]-1H-indole (Example 4e, 289.2 mg, 1.05 mmol) and 10% Pd/C (200 mg) in ethanol (3 mL) under $H_2$ at RT.

EXAMPLE 10

(a): 5-Fluoro-3-[(7R or 7S)(8a-R,S)-octahydrohydro-7-indolizinyl]-1-(2-naphthalenesulfonyl)indole, Isomer I To a solution of 5-Fluoro-3-[(7R or 7S)(8a-R,S)-octahydro-7-indolizinyl]-1H-indole, isomer I (Example 9b, 20 mg, 0.077 mmol) in THF (1 mL) at room temperature, was added sodium bis(trimethylsilyl)amide (1M solution in THF, 200 μL, 0.020 mmol) and the resulting solution was stirred for 5 minutes. 2-Naphthalenesulfonyl chloride (35 mg, 0.154 mmol) was then added and the solution stirred for 2 hours. Silica gel (2 g) and 2 drops water were then added to quench the reaction and the product was purified by silica gel chromatography to provide the title compound (27.1 mg, 78%).

(b) 5-Fluoro-3-[(7R or 7S)(8a-R,S)-octahydrohydro-7-indolizinyl]-1-(2-naphthalenesulfonyl)indole, Isomer II: (11.6 mg, 67%) from 5-fluoro-3-[(7R or 7S)(8a-R,S)-octahydro-7-indolizinyl]-1H-indole, Isomer II (Example 9c, 10 mg, 0.039 mmoles) and 2-naphthalenesulfonyl chloride (18 mg, 0.079 mmol) with 1M sodium bis(trimethylsilyl)amide (100 μL, 0.10 mmol) in THF (1 mL) at RT.

(c) 5-Fluoro-3-[(7R or 7S)(8a-R,S)-octahydrohydro-7-indolizinyl]-1-phenylsulfonylindole, Isomer I: (25.6 mg, 83%) from 5-fluoro-3-[(7R or 7S)(8a-R,S)-octahydro-7-indolizinyl]-1H-indole, Isomer I (Example 9b, 20 mg, 0.077 mmoles) and benzenesulfonyl chloride (20 μL, 0.016 mmol) with 1M sodium bis(trimethylsilyl)amide (200 μL, 0.20 mmol) in THF (1 mL) at RT.

(d) 5-Fluoro-3-[(7R or 7S)(8a-R,S)-octahydrohydro-7-indolizinyl]-1-phenylsulfonylindole, Isomer II: (9.0 mg, 58%) from 5-fluoro-3-[(7R or 7S)(8a-R,S)-octahydro-7-indolizinyl]-1H-indole, Isomer II (Example 9c, 10 mg, 0.039 mmoles) and benzenesulfonyl chloride (20 μL, 0.016 mmol) with 1M sodium bis(trimethylsilyl)amide (100 μL, 0.10 mmol) in THF (1 mL) at RT.

(e) 5-Fluoro-3-[(7R or 7S)(8a-R,S)-octahydrohydro-7-indolizinyl]-1-(1-napthalenesulfonyl)indole, Isomer I: (31.2 mg, 90%) from 5-fluoro-3-[(7R or 7S)(8a-R,S)-octahydro-7-indolizinyl]-1H-indole, Isomer I (Example 9b, 20 mg, 0.077 mmoles) and 1-naphthalenesulfonyl chloride (35 mg, 0.154 mmol) with 1M sodium bis(trimethylsilyl)amide (200 μL, 0.20 mmol) in THF (1 mL) at RT.

(f) 5-Fluoro-3-[(7R or 7S)(8a-R,S)-octahydrohydro-7-indolizinyl]-1-(1-naphthalenesulfonyl)indole, Isomer II: (13.4 mg, 77%) from 5-fluoro-3-[(7R or 7S)(8a-R,S)-octahydro-7-indolizinyl]-1H-indole, Isomer II (Example 9c, 10 mg, 0.039 mmoles) and 1-naphthalenesulfonyl chloride (18 mg, 0.079 mmol) with 1M sodium bis(trimethylsilyl)amide (100 μL, 0.10 mmol) in THF (1 mL) at RT.

(g) 5-Fluoro-3-[(7R or 7S)(8a-R,S)-octahydrohydro-7-indolizinyl]-1-(2,6-dichloro-benzoyl)indole, Isomer I: (29.8 mg, 90%) from 5-fluoro-3-[(7R or 7S)(8a-R,S)-octahydro-7-indolizinyl]-1H-indole, Isomer I (Example 9b, 20 mg, 0.078 mmol) and 2,6-dichlorobenzoyl chloride (32.4 mg, 0.154 mmol) with 1M sodium bis(trimethylsilyl)amide (200 μL, 0.20 mmoles) in THF (1 mL) at RT.

(h) 1-Benzyl-5-fluoro-3-[(7R or 7S)(8a-R,S)-octahydrohydro-7-indolizinyl]indole, Isomer I: (17.4 mg, 65%) from 5-fluoro-3-[(7R or 7S)(8a-R,S)-octahydrohydro-7-indolizinyl]-1H-indole, Isomer I (Example 9b, 20 mg, 0.078 mmol) and benzyl bromide (26 mg, 0.152 mmol) with 1M sodium bis(trimethylsilyl)amide (200 μL, 0.20 mmoles) in THF (1 mL) at RT.

(i) 5-Cyclohexyloxy-3-[(8a-R,S)-1,2,3,5,8,8a-hexahydrohydro-7-indolizinyl]-1-phenylsulfonylindole: (11.2 mg, 40%) from 5-cyclohexyloxy-3-[(8a-R,S)-1,2,3,5,8,8a-hexahydrohydro-7-indolizinyl]-1H-indole (20 mg, 0.0594 mmol) and benzenesulfonyl chloride (1.6 μL, 0.118 mmol) with 1M sodium bis(trimethylsilyl)amide (200 μL, 0.20 mmol) in THF (1 mL) at RT.

(j) 1-(2,5-Dichlorophenylsulfonyl)-5-Fluoro-3-[(7R or 7S)(8a-R,S)-octahydrohydro-7-indolizinyl]indole, Isomer I: (31.2 mg, 86%) from 5-fluoro-3-[(7R or 7S) (8a-R,S)-octahydro-7-indolizinyl]-1H-indole, Isomer I (Example 9b, 20 mg, 0.077 mmol) and 2,5-dichlorobenzenesulfonyl chloride (20 mg, 0.081 mmol) with 1M sodium bis(trimethylsilyl)amide (200 μL, 0.20 mmol) in THF (1 mL) at RT.

(k) 5-Fluoro-1-(3-methylphenylsulfonyl)-3-[(7R or 7S)(8a-R,S)octahydrohydro-7-indolizinyl]indole, Isomer I: (5.7 mg, 18%) from 5-fluoro-3-[(7R or 7S)(8a-R,S)-octahydro-7-indolizinyl]-1H-indole, Isomer I (Example 9b, 20 mg, 0.077 mmol) and 3-methylbenzenesulfonyl chloride (30 mg, 0.157 mmol) with 1M sodium bis(trimethylsilyl)amide (200 μL, 0.20 mmol) in THF (1 mL) at RT.

(l) 1-(2-Chlorobenzoyl)-5-fluoro-3-[(8a-R,S)-1,2,3,5,8,8a-hexahydro-7-indolizinyl)indole (17 mg, 55%): from 5-fluoro-3-[(8a-R,S)-1,2,3,5,8,8a-hexahydro-7-indolizinyl]-1H-indole (Example 4a, 20 mg, 0.078 mmol) and benzoyl chloride (27 mg, 0.154 mmol) with 1M sodium bis(trimethylsilyl)amide (200 μL, 0.20 mmol) in THF (1 mL) at RT.

(m) 5-Fluoro-1-[1-(2-naphthyl)methyl]-3-[(7R or 7S)(8a-R,S)-octahydro-7-indolizinyl)indole, Isomer I (4.5 mg, 15%): from 5-fluoro-3-[(7R or 7S)-octahydro-7-indolizinyl]-1H-indole, Isomer I (Example 9b, 20 mg, 0.077 mmol) and 2-(bromomethyl)naphthalene (35 mg, 0.158 mmol) with 1M sodium bis(trimethylsilyl)amide (200 μL, 0.20 mmol) in THF (1 mL) at RT.

(n) 5-Fluoro-1-(1-naphthoyl)-3-[(7R or 7S)(8a-R,S)-octahydro-7-indolizinyl]indole, Isomer I (9.3 mg, 29%): from 5-fluoro-3-[(7R or 7S)(8a-R,S)-octahydro-7-indolizinyl]-1H-indole, Isomer I (Example 9b, 20 mg, 0.077 mmoles) and naphthoyl chloride (29 mg, 0.153 mmol) with 1M sodium bis(trimethylsilyl)amide (200 μL, 0.20 mmol) in THF (1 mL) at RT.

(o) 5-Fluoro-1-[1-(1-naphthlyl)methyl]-3-[(7R or 7S)(8a-R,S)-octahydro-7-indolizinyl]indole, Isomer I (27.6 mg, 89%): from 5-fluoro-3-(octahydro-7-indolizinyl)-1H-indole, Isomer I (Example 9b, 20 mg, 0.077 mmoles) and 1-(chloromethyl)naphthalene (27 mg, 0.153 mmol) with 1M sodium bis(trimethylsilyl)amide (200 μL, 0.20 mmol) in THF (1 mL) at RT.

Summary of Exemplified Compounds of Formula I
| Ex. | R¹/R²/R³/R⁴ | R⁵ | R⁶/R⁷ | X | Z | n | —* |
|---|---|---|---|---|---|---|---|
| 6a | H | 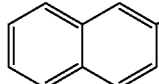 2-naphthyl-SO₂— | H | CH | N | 1 | sgl |
| 6b | H | 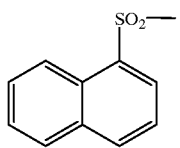 1-naphthyl-SO₂— | H | CH | N | 1 | sgl |
| 6c | H | 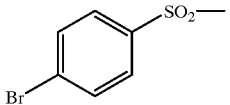 4-Br-C₆H₄-SO₂— | H | CH | N | 1 | sgl |
| 6d | H | 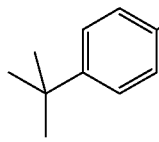 4-tBu-C₆H₄-SO₂— | H | CH | N | 1 | sgl |
| 6e | H | 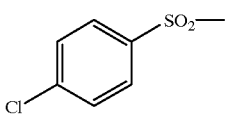 4-Cl-C₆H₄-SO₂— | H | CH | N | 1 | sgl |
| 6f | H | 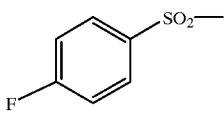 4-F-C₆H₄-SO₂— | H | CH | N | 1 | sgl |
| 6g | H | 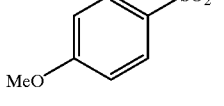 4-MeO-C₆H₄-SO₂— | H | CH | N | 1 | sgl |
| 6h | H | 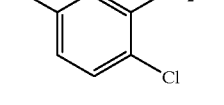 2,5-Cl₂-C₆H₃-SO₂— | H | CH | N | 1 | sgl |
| 6i | H | 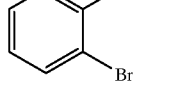 2-Br-C₆H₄-SO₂— | H | CH | N | 1 | sgl |
| 6j | H | 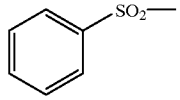 C₆H₅-SO₂— | H | CH | N | 1 | sgl |
| 6k | H | 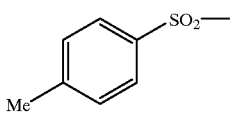 4-Me-C₆H₄-SO₂— | H | CH | N | 1 | sgl |

-continued
Summary of Exemplified Compounds of Formula I
| Ex. | R¹/R²/R³/R⁴ | R⁵ | R⁶/R⁷ | X | Z | n | —* |
|---|---|---|---|---|---|---|---|
| 6l | H | 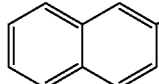 2-naphthyl-SO₂— | H | CH | N | 2 | sgl |
| 6m | H | 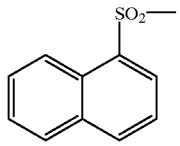 1-naphthyl-SO₂— | H | CH | N | 2 | sgl |
| 6n | H | 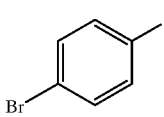 4-Br-C₆H₄-SO₂— | H | CH | N | 2 | sgl |
| 6o | H | 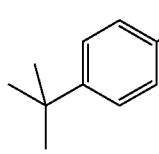 4-tBu-C₆H₄-SO₂— | H | CH | N | 2 | sgl |
| 6p | H | 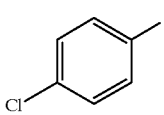 4-Cl-C₆H₄-SO₂— | H | CH | N | 2 | sgl |
| 6q | H | 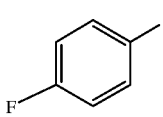 4-F-C₆H₄-SO₂— | H | CH | N | 2 | sgl |
| 6r | H | 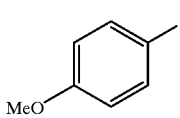 4-MeO-C₆H₄-SO₂— | H | CH | N | 2 | sgl |
| 6s | H | 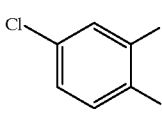 2,5-diCl-C₆H₃-SO₂— | H | CH | N | 2 | sgl |
| 6t | H | 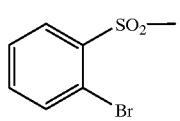 2-Br-C₆H₄-SO₂— | H | CH | N | 2 | sgl |
| 6u | H | 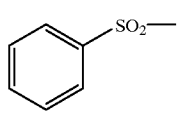 C₆H₅-SO₂— | H | CH | N | 2 | sgl |
| 6v | H | 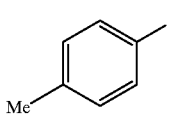 4-Me-C₆H₄-SO₂— | H | CH | N | 2 | sgl |

-continued

Summary of Exemplified Compounds of Formula I

| Ex. | R¹/R²/R³/R⁴ | R⁵ | R⁶/R⁷ | X | Z | n | —* |
|---|---|---|---|---|---|---|---|
| 6w | $R^2$ = F<br>$R^{1,3,4}$ = H | 2,4,6-trimethylphenyl-SO₂— | H | CH | N | 2 | sgl |
| 6x | $R^2$ = F<br>$R^{1,3,4}$ = H | phenyl-SO₂— | H | CH | C | 1 | dbl |
| 6y | $R^2$ = F<br>$R^{1,3,4}$ = H | naphthalen-1-yl-SO₂— | H | CH | C | 1 | dbl |
| 6z | $R^2$ = F<br>$R^{1,3,4}$ = H | naphthalen-2-yl-SO₂— | H | CH | C | 1 | dbl |
| 6aa | $R^2$ = F<br>$R^{1,3,4}$ = H | 4-fluorophenyl-SO₂— | H | CH | C | 1 | dbl |
| 6bb | $R^2$ = F<br>$R^{1,3,4}$ = H | 4-bromophenyl-SO₂— | H | CH | C | 1 | dbl |
| 6cc | $R^2$ = F<br>$R^{1,3,4}$ = H | 2-bromophenyl-SO₂— | H | CH | C | 1 | dbl |
| 6dd | $R^2$ = F<br>$R^{1,3,4}$ = H | 4-methylphenyl-SO₂— | H | CH | C | 1 | dbl |
| 6ee | $R^2$ = F<br>$R^{1,3,4}$ = H | 4-methoxyphenyl-SO₂— | H | CH | C | 1 | dbl |
| 6ff | $R^2$ = F<br>$R^{1,3,4}$ = H | 2,4,6-trimethylphenyl-SO₂— | H | CH | C | 1 | dbl |

-continued

Summary of Exemplified Compounds of Formula I

| Ex. | R¹/R²/R³/R⁴ | R⁵ | R⁶/R⁷ | X | Z | n | —* |
|---|---|---|---|---|---|---|---|
| 6gg | $R^2$ = F<br>$R^{1,3,4}$ = H | 4-tBu-C₆H₄-SO₂— | H | CH | C | 1 | dbl |
| 6hh | $R^2$ = F<br>$R^{1,3,4}$ = H | 2,5-diCl-C₆H₃-SO₂— | H | CH | C | 1 | dbl |
| 6ii | $R^2$ = F<br>$R^{1,3,4}$ = H | 4-Cl-C₆H₄-SO₂— | H | CH | C | 1 | dbl |
| 6jj | $R^{2,4}$ = F<br>$R^{1,3}$ = H | C₆H₅-SO₂— | H | CH | C | 1 | dbl |
| 6kk | $R^{2,4}$ = F<br>$R^{1,3}$ = H | 1-naphthyl-SO₂— | H | CH | C | 1 | dbl |
| 6ll | $R^{2,4}$ = F<br>$R^{1,3}$ = H | 2-naphthyl-SO₂— | H | CH | C | 1 | dbl |
| 6mm | $R^2$ = MeO<br>$R^{1,3,4}$ = H | C₆H₅-SO₂— | H | CH | C | 1 | dbl |
| 6nn | $R^2$ = MeO<br>$R^{1,3,4}$ = H | 1-naphthyl-SO₂— | H | CH | C | 1 | dbl |
| 6oo | $R^2$ = MeO<br>$R^{1,3,4}$ = H | 2-naphthyl-SO₂— | H | CH | C | 1 | dbl |
| 6pp | $R^2$ = Me<br>$R^{1,3,4}$ = H | C₆H₅-SO₂— | H | CH | C | 1 | dbl |

-continued

Summary of Exemplified Compounds of Formula I

| Ex. | R$^1$/R$^2$/R$^3$/R$^4$ | R$^5$ | R$^6$/R$^7$ | X | Z | n | —* |
|---|---|---|---|---|---|---|---|
| 6qq | R$^2$ = Me<br>R$^{1,3,4}$ = H | 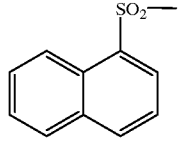 | H | CH | C | 1 | dbl |
| 6rr | R$^2$ = Me<br>R$^{1,3,4}$ = H | 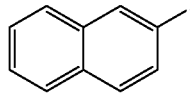 | H | CH | C | 1 | dbl |
| 6ss | R$^4$ = Me<br>R$^{1,2,3}$ = H | 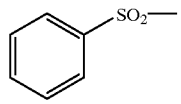 | H | CH | C | 1 | dbl |
| 6tt | R$^4$ = Me<br>R$^{1,2,3}$ = H | 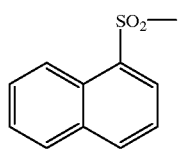 | H | CH | C | 1 | dbl |
| 6uu | R$^4$ = Me<br>R$^{1,2,3}$ = H | 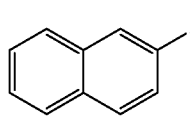 | H | CH | C | 1 | dbl |
| 7a | H | 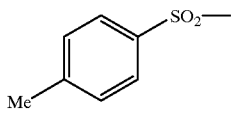 | H | N | N | 1 | sgl |
| 7b | H | 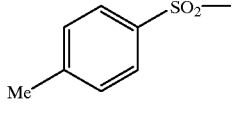 | H | N | N | 2 | sgl |
| 8 | R$^2$ = F<br>R$^{1,3,4}$ = H | 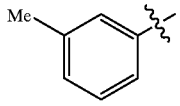 | H | CH | C | 1 | dbl |
| 9a | R$^2$ = F<br>R$^{1,3,4}$ = H | 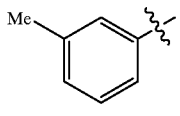 | H | CH | CH<br>(R,S) | 1 | sgl |
| 10a | R$^2$ = F<br>R$^{1,3,4}$ = H | 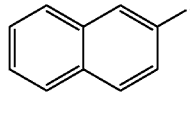 | H | CH | CH<br>R or S<br>Isomer<br>I | 1 | sgl |
| 10b | R$^2$ = F<br>R$^{1,3,4}$ = H | 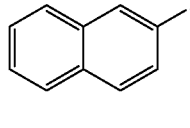 | H | CH | CH<br>R or S<br>Isomer<br>II | 1 | sgl |

-continued

Summary of Exemplified Compounds of Formula I

| Ex. | R¹/R²/R³/R⁴ | R⁵ | R⁶/R⁷ | X Z | n | —* |
|---|---|---|---|---|---|---|
| 10c | $R^2 = F$<br>$R^{1,3,4} = H$ | phenyl-SO₂— | H | CH CH<br>R or S<br>Isomer<br>I | 1 | sgl |
| 10d | $R^2 = F$<br>$R^{1,3,4} = H$ | phenyl-SO₂— | H | CH CH<br>R or S<br>Isomer<br>II | 1 | sgl |
| 10e | $R^2 = F$<br>$R^{1,3,4} = H$ | naphthyl-SO₂— | H | CH CH<br>R or S<br>Isomer<br>I | 1 | sgl |
| 10f | $R^2 = F$<br>$R^{1,3,4} = H$ | naphthyl-SO₂— | H | CH CH<br>R or S<br>Isomer<br>II | 1 | sgl |
| 10g | $R^2 = F$<br>$R^{1,3,4} = H$ | 2,6-dichlorophenyl-C(O)— | H | CH CH<br>Isomer<br>I | 1 | sgl |
| 10h | $R^2 = F$<br>$R^{1,3,4} = H$ | phenyl-CH₂— | H | CH CH<br>Isomer<br>I | 1 | sgl |
| 10i | $R^2 =$ cyclohexyl-O—<br>$R^{1,3,4} = H$ | phenyl-SO₂— | H | CH C | 1 | dbl |
| 10j | $R^2 = F$<br>$R^{1,3,4} = H$ | 2,5-dichlorophenyl-SO₂— | H | CH CH<br>R or S<br>Isomer<br>I | 1 | sgl |
| 10k | $R^2 = F$<br>$R^{1,3,4} = H$ | 3-Me-phenyl-SO₂— | H | CH CH<br>R or S<br>Isomer<br>I | 1 | Sgl |

-continued

Summary of Exemplified Compounds of Formula I

| Ex. | R¹/R²/R³/R⁴ | R⁵ | R⁶/R⁷ | X Z | n | —* |
|-----|-------------|-----|-------|-----|---|-----|
| 10l | $R^2 = F$<br>$R^{1,3,4} = H$ | 2-chlorobenzoyl | H | CH C | 1 | Dbl |
| 10m | $R^2 = F$<br>$R^{1,3,4} = H$ | 2-naphthylmethyl | H | CH CH<br>Isomer I | 1 | sgl |
| 10n | $R^2 = F$<br>$R^{1,3,4} = H$ | 1-naphthoyl | H | CH CH<br>Isomer I | 1 | sgl |
| 10o | $R^2 = F$<br>$R^{1,3,4} = H$ | 1-naphthylmethyl | H | CH CH<br>Isomer I | 1 | sgl |

*sgl = single bond; dbl = double bond

EXAMPLE 11
Binding Affinity for the 5-HT$_6$ Receptor

All of the compounds of the invention were evaluated using cell types receptive specifically to the 5-HT$_6$ receptor (for cloning and characterization of the human 5-HT$_6$ receptor see Kohen, et al. J. Neurochemistry, 66, 1996: 47–56). The assay protocol generally entailed the incubation of membranes prepared from cells expressing the 5-HT$_6$ receptor with $^3$H-LSD (2 nM). Increasing levels of the test compound were incubated with the radioligand and the membrane homogenates prepared from the recombinant cells. After a 60 minute incubation at 37° C., the incubation was terminated by vacuum filtration. The filters were washed with buffer and the filters were counted for radioactivity using liquid scintillation spectrometry. The affinity of the test compound for the 5-HT$_6$ receptor was determined by computer-assisted analysis of the data and determining the amount of the compound necessary to inhibit 50% of the binding of the radioligand to the receptor. Concentrations ranging from $10^{-11}$ M to $10^{-5}$ M of the test compound were evaluated. For comparison, the affinity of clozapine (Ki=3 nM) for the 5-HT$_6$ receptor was used as a standard. Affinity for the 5-HT$_6$ receptor is expressed as the amount (in percent) of binding of the radioligand that is inhibited in the presence of 100 nM of test compound. A greater percent inhibition indicates greater affinity for the 5-HT$_6$ receptor. Selected compounds of the invention showed an percent inhibition of greater than 50% for the 5-HT$_6$ receptor. Specific compounds of the invention, for example, those of examples 6a, 6b, 6c, 6d, 6e, 6f, 6g, 6g, 6h, 6i, 6j, 6k, 6l, 6m, 6n, 6p, 6u, 6v, 6x, 6y, 6z, 6aa, 6bb, 6cc, 6dd, 6ee, 6gg, 6hh, 6ii, 6jj, 6kk, 6ll, 6mm, 6nn, 6oo, 6pp, 6qq, 6rr, 6ss, 6tt, 6jj, 6kk, 7a, 7b, 9a, 10a, 10b, 10c, 10d, 10e, 10f, 10h, 10i, 10j and 10k, showed an percent inhibition of greater than 80% for the 5-HT$_6$ receptor. More specific compounds of the invention, for example, those of examples 6a, 6b, 6c, 6d, 6e, 6f, 6g, 6g, 6h, 6i, 6j, 6k, 6l, 6m, 6v, 6x, 6y, 6z, 6aa, 6bb, 6cc, 6dd, 6ii, 6jj, 6kk, 6mm, 6nn, 6oo, 6pp, 6qq, 6rr, 6jj, 6kk, 7a, 9a, 10e, 10f and 10i, showed an percent inhibition of greater than 95% for the 5-HT$_6$ receptor. In terms of selectivity, selected compounds of the invention showed an percent inhibition of greater than 50% for the 5-HT$_6$ receptor and also had an percent inhibition less than 50% for other serotonin receptors, specifically the 5-HT$_{2A}$, 5HT$_{2C}$ and 5-HT$_7$ receptors. Specific compounds, for example those of examples 6a, 6b, 6c, 6d, 6g, 6j, 6l, 6m, 6n, 6p, 6u, 6x, 6y, 6z, 6aa, 6bb, 6cc, 6dd, 6ee, 6gg, 6hh, 6ii, 6ll, 6mm, 6nn, 6oo, 6pp, 6qq, 6rr, 6ss, 6tt, 6jj, 6kk, 10f and 10b showed an percent inhibition of greater than 80% for the 5-HT$_6$ receptor and less than 20% for the 5-HT$_{2A}$, 5HT$_{2C}$ and 5-HT$_7$ receptors. More specific compounds, for example those of examples 6m, 6x, 6z, 6ll, 6mm, 6nn, 6oo, 6pp, 6qq, 6rr, 6jj and 10b showed an percent inhibition of greater than 90% for the 5-HT$_6$ receptor and less than 10% for the 5-HT$_{2A}$, 5HT$_{2C}$ and 5-HT$_7$ receptors

EXAMPLE 12
Functional Assay

The 5HT$_6$ receptor responds to serotonin and other agonists by increasing adenyl cyclase mediated production of cyclic AMP. Particular test compounds were assayed for their effect on adenyl cyclase activity using the procedure described below.

Compounds acting as antagonists at the 5HT$_6$ receptor will antagonize the agonist effect of serotonin and thus, will block the serotonin-induced increase in adenyl cyclase activity.

HEK 293 cells stably expressing the human 5HT$_6$ receptor were plated in 6 well plates in DMEM (Dulbecco's Modified Eagle Medium)/F12 (Nutrient Mixture F12-Ham)

media with 10% FCS (fetal calf serum) and G418 (Geneticen Disulfate, 500 ug/ml), and incubated at 37° C. in a $CO_2$ incubator. The cells were allowed to grow to about 70% confluence before use in the assay.

The culture medium of each well was removed, and the wells were washed once with serum free media. Then 2 ml of SFM+IBMX medium (SFM with 0.5 mM IBMX, 3-isobutyl-1-methylxanthine, 0.1% ascorbic acid and 10 mM pargyline) was added to each well and the wells were incubated at 37° C. for 10 min. Following incubation, the SFM+IBMX medium was removed from each well and fresh SFM+IBMX media was added to the wells separately with one of a) serotonin (1 μM final concentration); b) test compound (100 nM and 10 μM, to test for agonist activity); and c) test compound (100 nM and 10 μM) along with serotonin (μM final concentration, to test for antagonist activity). Basal adenyl cyclase activity was determined from wells with only SFM+IBMX media added.

The cells were then incubated at 37° C. for 30 minutes in a $CO_2$ incubator. Following incubation, the media were removed from each well. The wells were washed once with 1 ml of PBS (phosphate buffered saline). Each well was then treated with 1 mL cold 95% ethanol:5 mM EDTA (2:1) at 4° C. for 1 hour. The cells from each well were then scraped and transferred into individual Eppendorf tubes. The tubes were centrifuged for 5 minutes at 4° C., and the supernatants were transferred to new Eppendorf tubes and stored at 4° C. The pellets were discarded and the supernatants were stored at 4° C. until assayed for cAMP concentration. cAMP content for each extract was determined in duplicate by EIA (enzyme-immunoassay) using the Amersham Biotrak cAMP EIA kit (Amersham RPN 225). Final results were expressed as % basal response for agonists and % reversal of serotonin response for antagonists.

The total stimulation of adenyl cyclase by serotonin ($S_o$) was determined as the difference in concentration of cAMP in the serotonin-treated cells ($C_d$) and the basal-treated cells ($C_f$).

$$S_o = C_f - C_d$$

The net stimulation (S) of basal adenyl cyclase by an agonist test compound was determined as the difference in cAMP concentration in the drug-treated cell (C) and the basal-treated cells ($C_f$).

$$S = C_f - C$$

The net stimulation ($S_s$) of basal adenyl cyclase by serotonin in the presence of an antagonist test compound was determined as the difference in cAMP concentration in the serontonin-drug-treated cells ($C_s$) and the basal-treated cells ($C_f$).

$$S_s = C_f - C_s$$

The ability of the antagonist test compound to reverse the serotonin stimuation of adenyl cyclase activity (% reversal, % R) was determined by the formula:

$$\%R = (1 - S_s/S_o) \times 100$$

Selected compounds of the invention, for example those of Examples 6x, 6y, 10c, 10e, 10a, 10d, 10f, 10b, 6b and 6j, were able to reverse the serotonin stimulation of adenyl cyclase and thus were shown to behave as a $5\text{-HT}_6$ receptor antagonist.

We claim:

1. A compound according to Formula I and a salt, solvate or hydrate thereof:

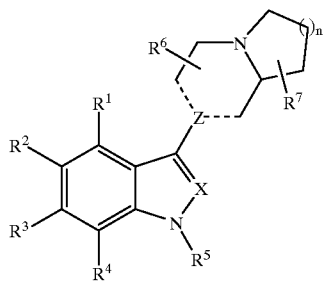

wherein:
$R^1$, $R^2$, $R^3$ and $R^4$ are independently selected from the group consisting of H, halo, OH, $C_{1-6}$alkyl, $C_{1-6}$alkoxy, $C_{2-6}$alkenyl, $C_{2-6}$alkynyl, $C_{3-7}$cycloalkyl, $C_{4-7}$cycloalkenyl, $C_{3-7}$cycloalkoxy, $C_{3-7}$cycloalkylthio, halo-substituted-$C_{1-6}$alkyl, $C_{1-6}$alkylthio, $C_{2-7}$alkanoyl, $C_{2-7}$alkanoyloxy, nitro, cyano, optionally substituted phenyl, optionally substituted furanyl, optionally substituted thienyl, optionally substituted phenyloxy, $NR^8R^9$, $C(O)NR^8R^9$, $SO_2NR^8R^9$, $CH_2SO_2NR^8R^9$, $CO_2R^{10}$, NHC$(O)R^{11}$, $NHC(NR^{12})R^{11}$, $C(NR^{13})NR^{14}R^{15}$, $C(O)R^{16}$, $OC(O)R^{16}$, $SCF_3$, $SO_2CF_3$, formyl, $CF_3$ and $CF_3O$;

$R^5$ is selected from the group consisting of $SO_2Ar$, C(O)Ar, $CH_2Ar$ and Ar;

$R^6$ is independently selected from the group consisting of H, $C_{1-6}$alkyl, optionally substituted phenyl and optionally substituted benzyl $R^7$ is independently selected from the group consisting of H, $C_{1-6}$alkyl, $C_{1-6}$alkoxy, $C_{1-6}$alkylthio, optionally substituted phenyl, optionally substituted benzyl, optionally substituted phenoxy and optionally substituted benzyloxy;

— — — — — represents a single or double bond;

n is selected from an integer of from 1–3;

X is selected from the group consisting of $CR^{17}$ and N;

Z is selected from the group consisting of C, CH and N, provided that when — — — — — is a double bond, Z is C and when — — — — — is a single bond, Z is selected from CH and N;

Ar is an optionally substituted aromatic group selected from the group consisting of phenyl, pyridyl, thienyl, furanyl, naphthyl, quinolyl and isoquinolyl wherein the optional substituents are independently selected from 1–4 members of the group consisting of halo, OH, $C_{1-6}$alkyl, $C_{1-6}$alkoxy, $C_{1-6}$alkylthio, $CF_3$ and $CF_3O$;

$R^8$, $R^9$ and $R^{10}$ are independently selected from the group consisting of H, $C_{1-6}$alkyl and phenyl or $R^8$ and $R^9$ may form an alkylene chain, —$(CH_2)_m$—, where m=3–6, to form, together with the nitrogen to which they are attached a 4- to 7-membered ring;

$R^{11}$ is selected from the group consisting of $C_{1-6}$alkyl, $C_{1-6}$alkoxy, phenyl, phenoxy, $NH_2$, alkylamino, dialkylamino, benzyl and benzyloxy;

$R^{12}$ is selected from the group consisting of H and $C_{1-6}$alkyl;

$R^{13}$ is selected from the group consisting of H and $C_{1-6}$alkyl;

$R^{14}$ and $R^{15}$ are independently selected from the group consisting of H and $C_{1-6}$alkyl or one of $R^{14}$ and $R^{15}$, together with $R^{13}$, forms an alkylene chain, —$(CH_2)_p$—, where p=2 or 3, bridging the nitrogen atoms to which they are attached;

$R^{16}$ is selected from the group consisting of optionally substituted phenyl, optionally substituted pyridyl, optionally substituted thienyl, optionally substituted furanyl and optionally substituted naphthyl; and $R^{17}$ is selected from the group consisting of H, $C_{1-6}$alkyl and benzyl.

2. A compound according to claim 1 wherein $R^1$, $R^3$ and $R^4$ are all H.

3. A compound according to claim 1, wherein $R^1$ and $R^3$ are both H and $R^2$ and $R^4$ are independently selected from the group consisting of H, halo, $C_{1-6}$alkyl, $C_{1-6}$alkoxy, $CF_3$ and $CF_3O$.

4. A compound according to claim 3, wherein $R^4$ is H.

5. A compound according to claim 4 wherein $R^2$ is independently selected from the group consisting of H, fluoro, methyl and methoxy.

6. A compound according to claim 3, wherein $R^2$ and $R^4$ are both fluoro.

7. A compound according to claim 3, wherein $R^2$ is H and $R^4$ is $C_{1-6}$alkyl.

8. A compound according to claim 3, wherein $R^4$ is methyl.

9. A compound according to claim 1, wherein $R^1$–$R^4$ are all H.

10. A compound according to claim 3, wherein $R^6$ and $R^7$ are both H.

11. A compound according to claim 3, wherein X is selected from CH and N.

12. A compound according to claim 11, wherein X is CH.

13. A compound according to claim 3, wherein Z, and n are selected to form ring systems selected from 1,4-diaza[4.3.0]bicyclononane, 1,4-diaza[4.4.0]bicyclodecane, 1,2,3,5,8,8a-hexahydroindolizine and octahydroindolizine.

14. A compound according to claim 13, wherein $R^6$ and $R^7$ are both H.

15. A compound according to claim 3, wherein $R^5$ is selected from $SO_2Ar$ and Ar, wherein Ar is an optionally substituted aromatic group selected from the group consisting of phenyl, pyridyl, thienyl, furanyl, naphthyl, quinolyl and isoquinolyl wherein the optional substituents are independently selected from 1–3 members of the group consisting of halo, OH, $C_{1-6}$alkyl, $C_{1-6}$alkoxy, $C_{1-6}$alkylthio, $CF_3$ and $CF_3O$.

16. A compound according to claim 15, wherein $R^5$ is $SO_2Ar$.

17. A compound according to claim 16, wherein Ar is an optionally substituted aromatic group selected from phenyl and naphthyl, wherein the optional substituents are independently selected from 1–3 members of the group consisting of halo, OH, $C_{1-6}$alkyl, $C_{1-6}$alkoxy, $C_{1-6}$alkylthio, $CF_3$ and $CF_3O$.

18. A compound according to claim 17, wherein Ar is unsubstituted naphthyl.

19. A compound according to claim 18, wherein Ar is selected from 1-naphthyl and 2-naphthyl.

20. A compound according to claim 17, wherein Ar is selected from unsubstituted phenyl and phenyl substituted with 1–3 substituents optionally selected from $C_{1-6}$alkyl, halo and $C_{1-6}$alkoxy.

21. A compound according to claim 20 wherein Ar is selected from phenyl, 4-bromophenyl, 4-t-butylphenyl, 4-chlorophenyl, 4-fluorophenyl, 4-methoxyphenyl, 2,5-dichlorophenyl, 2-bromophenyl, 4-methylphenyl and 2,4,6-trimethylphenyl.

22. A compound according to claim 1, which is selected from the group consisting of:

3-[(6-R,S)-1,4-Diaza[4.3.0]bicyclonon-4-yl)]-1-(2-naphthalenesulfonyl)indole;
3-[(6-R,S)-1,4-Diaza[4.3.0]bicyclonon-4-yl]-1-(1-naphthalenesulfonyl)indole;
1-(4-Bromophenylsulfonyl)-3-[(6-R,S)-1,4-diaza[4.3.0]bicyclonon-4-yl]indole;
1-(4-t-Butylphenylsulfonyl)-3-[(6-R,S)-1,4-diaza[4.3.0]bicyclonon-4-yl]indole;
1-(4-Chlorophenylsulfonyl)-3-[(6-R,S)-1,4-diaza[4.3.0]bicyclonon-4-yl]indole;
3-[(6-R,S)-1,4-Diaza[4.3.0]bicyclonon-4-yl]-1-(4-fluorophenylsulfonyl)indole;
3-[(6-R,S)-1,4-Diaza[4.3.0]bicyclonon-4-yl]-1-(4-methoxyphenylsulfonyl)indole;
3-[(6-R,S)-1,4-Diaza[4.3.0]bicyclonon-4-yl]-1-(2,5-dichlorophenylsulfonyl)indole;
1-(2-Bromophenylsulfonyl)-3-[(6-R,S)-1,4-diaza[4.3.0]bicyclonon-4-yl]indole;
3-[(6-R,S)-1,4-Diaza[4.3.0]bicyclonon-4-yl]-1-(phenylsulfonyl)indole;
3-[(6-R,S)-1,4-Diaza[4.3.0]bicyclonon-4-yl]-1-(4-methylphenylsulfonyl)indole;
3-[(6-R,S)-1,4-Diaza[4.4.0]bicyclodecan-4-yl]-1-(2-naphthalenesulfonyl)indole;
3-[(6-R,S)-1,4-Diaza[4.4.0]bicyclodecan-4-yl]-1-(1-naphthalenesulfonyl)indole;
1-(4-Bromophenylsulfonyl)-3-[(6-R,S)-1,4-diaza[4.4.0]bicyclodecan-4-yl]indole;
1-(4-t-Butylphenylsulfonyl)-3-[(6-R,S)-1,4-diaza[4.4.0]bicyclodecan-4-yl]indole;
1-(4-Chlorophenylsulfonyl)-3-[(6-R,S)-1,4-diaza[4.4.0]bicyclodecan-4-yl]indole;
3-[(6-R,S)-1,4-Diaza[4.4.0]bicyclodecan-4-yl]-1-(4-fluorophenylsulfonyl)indole;
3-[(6-R,S)-1,4-Diaza[4.4.0]bicyclodecan-4-yl]-1-(4-methoxyphenylsulfonyl)indole;
3-[(6-R,S)-1,4-Diaza[4.4.0]bicyclodecan-4-yl]-1-(2,5-dichlorophenylsulfonyl)indole;
1-(2-Bromophenylsulfonyl)-3-[(6-R,S)-1,4-diaza[4.4.0]bicyclodecan-4-yl]indole;
3-[(6-R,S)-1,4-Diaza[4.4.0]bicyclodecan-4-yl]-1-(phenylsulfonyl)indole;
3-[(6-R,S)-1,4-Diaza[4.4.0]bicyclodecan-4-yl]-1-(4-methylphenylsulfonyl)indole;
3-[(6-R,S)-1,4-Diaza[4.4.0]bicyclodecan-4-yl]-1-(2,4,6-trimethyl phenylsulfonyl)indole;
5-Fluoro-3-[(8a-R,S)-1,2,3,5,8,8a-hexahydro-7-indolizinyl]-1-phenylsulfonylindole;
5-Fluoro-3-[(8a-R,S)-1,2,3,5,8,8a-hexahydro-7-indolizinyl]-1-(1-naphthalenesulfonyl)indole;
5-Fluoro-3-[(8a-R,S)-1,2,3,5,8,8a-hexahydro-7-indolizinyl]-1-(2-naphthalenesulfonyl)indole;
5-Fluoro-1-(4-fluorophenylsulfonyl)-3-[(8a-R,S)-1,2,3,5,8,8a-hexahydro-7-indolizinyl]indole;
1-(4-Bromophenylsulfonyl)-5-fluoro-3-[(8a-R,S)-1,2,3,5,8,8a-hexahydro-7-indolizinyl]indole;
1-(2-Bromophenylsulfonyl)-5-fluoro-3-[(8a-R,S)-1,2,3,5,8,8a-hexahydro-7-indolizinyl]indole;
5-Fluoro-3-[(8a-R,S)-1,2,3,5,8,8a-hexahydro-7-indolizinyl]-1-(4-methylphenylsulfonyl)indole;
5-Fluoro-3-[(8a-R,S)-1,2,3,5,8,8a-hexahydro-7-indolizinyl]-1-(4-methoxyphenylsulfonyl)indole;
5-Fluoro-3-[(8a-R,S)-1,2,3,5,8,8a-hexahydro-7-indolizinyl]-1-(2,4,6-trimethylphenylsulfonyl)indole;
1-(4-t-Butylphenylsulfonyl)-5-fluoro-3-[(8a-R,S)-1,2,3,5,8,8a-hexahydro-7-indolizinyl]indole;
1-(2,5-Dichlorophenylsulfonyl)-5-fluoro-3-[(8a-R,S)-1,2,3,5,8,8a-hexahydro-7-indolizinyl]indole;
1-(4-Chlorophenylsulfonyl)-5-fluoro-3-[(8a-R,S)-1,2,3,5,8,8a-hexahydro-7-indolizinyl]indole;
3-[(6-R,S)-1,4-Diaza[4.3.0]bicyclonon-4-yl]-1-(4-methylphenylsulfonyl)indazole;

3-[(6-R,S)-1,4-Diaza[4.4.0]bicyclodecan-4-yl]-1-(4-methylphenylsulfonyl)indazole;
5,7-Difluoro-3-[(8a-R,S)-1,2,3,5,8,8a-hexahydro-7-indolizinyl]-1-phenylsulfonylindole;
5,7-Difluoro-3-[(8a-R,S)-1,2,3,5,8,8a-hexahydro-7-indolizinyl]-1-naphthalenesulfonylindole;
5,7-Difluoro-3-[(8a-R,S)-1,2,3,5,8,8a-hexahydro-7-indolizinyl]-2-naphthalenesulfonylindole;
5-Methoxy-3-[(8a-R,S)-1,2,3,5,8,8a-hexahydro-7-indolizinyl]-1-phenylsulfonylindole;
5-Methoxy-3-[(8a-R,S)-1,2,3,5,8,8a-hexahydro-7-indolizinyl]-1-naphthalenesulfonylindole;
5-Methoxy-3-[(8a-R,S)-1,2,3,5,8,8a-hexahydro-7-indolizinyl]-2-naphthalenesulfonylindole;
5-Methyl-3-[(8a-R,S)-1,2,3,5,8,8a-hexahydro-7-indolizinyl]-1-phenylsulfonylindole;
5-Methyl-3-[(8a-R,S)-1,2,3,5,8,8a-hexahydro-7-indolizinyl]-1-naphthalenesulfonylindole;
5-Methyl-3-[(8a-R,S)-1,2,3,5,8,8a-hexahydro-7-indolizinyl]-2-naphthalenesulfonylindole;
7-Methyl-3-[(8a-R,S)-1,2,3,5,8,8a-hexahydro-7-indolizinyl]-1-phenylsulfonylindole;
7-Methyl-3-[(8a-R,S)-1,2,3,5,8,8a-hexahydro-7-indolizinyl]-1-naphthalenesulfonylindole;
7-Methyl-3-[(8a-R,S)-1,2,3,5,8,8a-hexahydro-7-indolizinyl]-2-naphthalenesulfonylindole;
5-Fluoro-3-(1,2,3,5,8,8a-hexahydrohydro-7-indolizinyl)-1-(3-methylphenyl)indole;
5-Fluoro-3-[(7-R,S)(8a-R,S)-octahydro-7-indolizinyl]-1-(3-methylphenyl)indole;
5-Fluoro-3-[(7R or 7S)(8a-R,S)-octahydrohydro-7-indolizinyl]-1-(2-naphthalenesulfonyl)indole, Isomer I;
5-Fluoro-3-[(7R or 7S)(8a-R,S)-octahydrohydro-7-indolizinyl]-1-(2-naphthalenesulfonyl)indole, Isomer II;
5-Fluoro-3-[(7R or 7S)(8a-R,S)-octahydrohydro-7-indolizinyl]-1-phenylsulfonylindole, Isomer II;
5-Fluoro-3-[(7R or 7S)(8a-R,S)-octahydrohydro-7-indolizinyl]-1-phenylsulfonylindole, Isomer II;
5-Fluoro-3-[(7R or 7S)(8a-R,S)-octahydrohydro-7-indolizinyl]-1-(1-naphthalenesulfonyl)indole, Isomer I;
5-Fluoro-3-[(7R or 7S)(8a-R,S)-octahydrohydro-7-indolizinyl]-1-(1-naphthalenesulfonyl)indole, Isomer II;
5-Fluoro-3-[(7R or 7S)(8a-R,S)-octahydrohydro-7-indolizinyl]-1-(2,6-dichloro-benzoyl)indole Isomer II;
1-Benzyl-5-fluoro-3-[(7R or 7S)(8a-R,S)-octahydrohydro-7-indolizinyl]indole, Isomer I;
5-Cyclohexyloxy-3-[(8a-R,S)-1,2,3,5,8,8a-hexahydrohydro-7-indolizinyl]-1-phenylsulfonylindole;
1-(2,5-Dichlorophenylsulfonyl)-5-Fluoro-3-[(7R or 7S)(8a-R,S)-octahydrohydro-7-indolizinyl]indole, Isomer I;
5-Fluoro-1-(3-methylphenylsulfonyl)-3-[(7R or 7S)(8a-R,S) octahydrohydro-7-indolizinyl]]indole, Isomer I;
1-(2-Chlorobenzoyl)-5-fluoro-3-[(8a-R,S)-1,2,3,5,8,8a-hexahydro-7-indolizinyl]indole;
5-Fluoro-1-[1-(2-naphthyl)methyl]-3-[(7R or 7S)(8a-R,S)-octahydro-7-indolizinyl]indole, Isomer I;
5-Fluoro-1-(1-naphthoyl)-3-[(7R or 7S)(8a-R,S)-octahydro-7-indolizinyl]indole, Isomer I; and
5-Fluoro-1-[1-(1-naphthlyl)methyl]-3-[(7R or 7S)(8a-R,S)-octahydro-7-indolizinyl]indole, Isomer I.

23. A compound according to claim 22, which is selected from the group consisting of:

3-[(6-R,S)-1,4-Diaza[4.3.0]bicyclonon-4-yl]-1-(2-naphthalenesulfonyl)indole;
3-[(6-R,S)-1,4-Diaza[4.3.0]bicyclonon-4-yl]-1-(1-naphthalenesulfonyl)indole;
1-(4-Bromophenylsulfonyl)-3-[(6-R,S)-1,4-diaza[4.3.0]bicyclonon-4-yl]indole;
1-(4-t-Butylphenylsulfonyl)-3-[(6-R,S)-1,4-diaza[4.3.0]bicyclonon-4-yl]indole;
3-[(6-R,S)-1,4-Diaza[4.3.0]bicyclonon-4-yl]-1-(4-methoxyphenylsulfonyl)indole;
3-[(6-R,S)-1,4-Diaza[4.3.0]bicyclonon-4-yl]-1-(phenylsulfonyl)indole;
3-[(6-R,S)-1,4-Diaza[4.3.0]bicyclonon-4-yl]-1-(4-methylphenylsulfonyl)indole;
3-[(6-R,S)-1,4-Diaza[4.4.0]bicyclodecan-4-yl]-1-(2-naphthalenesulfonyl)indole;
3-[(6-R,S)-1,4-Diaza[4.4.0]bicyclodecan-4-yl]-1-(1-naphthalenesulfonyl)indole;
1-(4-Bromophenylsulfonyl)-3-[(6-R,S)-1,4-diaza[4.4.0]bicyclodecan-4-yl]indole;
1-(4-Chlorophenylsulfonyl )-3-[(6-R,S)-1,4-diaza[4.4.0]bicyclodecan-4-yl]indole;
3-[(6-R,S)-1,4-Diaza[4.4.0]bicyclodecan-4-yl]-1-(phenylsulfonyl)indole;
3-[(6-R,S)-1,4-Diaza[4.4.0]bicyclodecan-4-yl]-1-(4-methylphenylsulfonyl)indole;
5-Fluoro-3-[(8a-R,S)-1,2,3,5,8,8a-hexahydro-7-indolizinyl]-1-phenylsulfonylindole;
5-Fluoro-3-[(8a-R,S)-1,2,3,5,8,8a-hexahydro-7-indolizinyl]-1-(1-naphthalenesulfonyl)indole;
5-Fluoro-3-[(8a-R,S)-1,2,3,5,8,8a-hexahydro-7-indolizinyl]-1-(2-naphthalenesulfonyl)indole;
5-Fluoro-1-(4-fluorophenylsulfonyl)-3-[(8a-R,S)-1,2,3,5,8,8a-hexahydro-7-indolizinyl]indole;
1-(4-Bromophenylsulfonyl)-5-fluoro-3-[(8a-R,S)-1,2,3,5,8,8a-hexahydro-7-indolizinyl]indole;
1-(2-Bromophenylsulfonyl)-5-fluoro-3-[(8a-R,S)-1,2,3,5,8,8a-hexahydro-7-indolizinyl]indole;
5-Fluoro-3-[(8a-R,S)-1,2,3,5,8,8a-hexahydro-7-indolizinyl]-1-(4-methylphenylsulfonyl)indole;
5-Fluoro-3-[(8a-R,S)-1,2,3,5,8,8a-hexahydro-7-indolizinyl]-1-(4-methoxyphenylsulfonyl)indole;
1g-(4-t-Butylphenylsulfonyl)-5-fluoro-3-[(8a-R,S)-1,2,3,5,8,8a-hexahydro-7-indolizinyl]indole;
1-(2,5-Dichlorophenylsulfonyl)-5-fluoro-3-[(8a-R,S)-1,2,3,5,8,8a-hexahydro-7-indolizinyl]indole;
1-(4-Chlorophenylsulfonyl)-5-fluoro-3-[(8a-R,S)-1,2,3,5,8,8a-hexahydro-7-indolizinyl]indole;
5,7-Difluoro-3-[(8a-R,S)-1,2,3,5,8,8a-hexahydro-7-indolizinyl]-1-phenylsulfonylindole;
5,7-Difluoro-3-[(8a-R,S)-1,2,3,5,8,8a-hexahydro-7-indolizinyl]-1-naphthalenesulfonylindole;
5,7-Difluoro-3-[(8a-R,S)-1,2,3,5,8,8a-hexahydro-7-indolizinyl]-2-naphthalenesulfonylindole;
5-Methoxy-3-[(8a-R,S)-1,2,3,5,8,8a-hexahydro-7-indolizinyl]-1-phenylsulfonylindole;
5-Methoxy-3-[(8a-R,S)-1,2,3,5,8,8a-hexahydro-7-indolizinyl]-1-naphthalenesulfonylindole;
5-Methoxy-3-[(8a-R,S)-1,2,3,5,8,8a-hexahydro-7-indolizinyl]-2-naphthalenesulfonylindole;
5-Methyl-3-[(8a-R,S)-1,2,3,5,8,8a-hexahydro-7-indolizinyl]-1-phenylsulfonylindole;
5-Methyl-3-[(8a-R,S)-1,2,3,5,8,8a-hexahydro-7-indolizinyl]-1-naphthalenesulfonylindole;
5-Methyl-3-[(8a-R,S)-1,2,3,5,8,8a-hexahydro-7-indolizinyl]-2-naphthalenesulfonylindole;
7-Methyl-3-[(8a-R,S)-1,2,3,5,8,8a-hexahydro-7-indolizinyl]-1-phenylsulfonylindole;
7-Methyl-3-[(8a-R,S)-1,2,3,5,8,8a-hexahydro-7-indolizinyl]-1-naphthalenesulfonylindole;
5-Fluoro-3-[(7R or 7S)(8a-R,S)-octahydrohydro-7-indolizinyl]-1-(2-naphthalenesulfonyl)indole, Isomer II; and 5-Fluoro-3-[(7R or 7S)(8a-R,S)-octahydrohydro-7-indolizinyl]-1-(1-naphthalenesulfonyl)indole, Isomer II.

24. A compound according to claim 23, which is selected from the group consisting of:

3-[(6-R,S)-1,4-Diaza[4.4.0]bicyclodecan-4-yl]-1-(1-naphthalenesulfonyl)indole;
5-Fluoro-3-[(8a-R,S)-1,2,3,5,8,8a-hexahydro-7-indolizinyl]-1-phenylsulfonylindole;
5-Fluoro-3-[(8a-R,S)-1,2,3,5,8,8a-hexahydro-7-indolizinyl]-1-(2-naphthalenesulfonyl)indole;
5,7-Difluoro-3-[(8a-R,S)-1,2,3,5,8,8a-hexahydro-7-indolizinyl]-2-naphthalenesulfonylindole;
5-Methoxy-3-[(8a-R,S)-1,2,3,5,8,8a-hexahydro-7-indolizinyl]-1-phenylsulfonylindole;
5-Methoxy-3-[(8a-R,S)-1,2,3,5,8,8a-hexahydro-7-indolizinyl]-1-naphthalenesulfonylindole;
5-Methoxy-3-[(8a-R,S)-1,2,3,5,8,8a-hexahydro-7-indolizinyl]-2-naphthalenesulfonylindole;
5-Methyl-3-[(8a-R,S)-1,2,3,5,8,8a-hexahydro-7-indolizinyl]-1-phenylsulfonylindole;
5-Methyl-3-[(8a-R,S)-1,2,3,5,8,8a-hexahydro-7-indolizinyl]-1-naphthalenesulfonylindole;
5-Methyl-3-[(8a-R,S)-1,2,3,5,8,8a-hexahydro-7-indolizinyl]-2-naphthalenesulfonylindole;
5,7-Difluoro-3-[(8a-R,S)-1,2,3,5,8,8a-hexahydro-7-indolizinyl]-1-phenylsulfonylindole; and
5-Fluoro-3-[(7R or 7S)(8a-R,S)-octahydrohydro-7-indolizinyl]-1-(2-naphthalenesulfonyl)indole, Isomer II.

25. A pharmaceutical composition, comprising a pharmaceutically acceptable carrier and, in an amount effective to antagonize the 5-HT$_6$ receptor, a compound of claim 1.

26. A pharmaceutical composition, comprising a pharmaceutically acceptable carrier and, in an amount effective to antagonize the 5-HT$_6$ receptor, a compound of according to claim 3.

27. A pharmaceutical composition, comprising a pharmaceutically acceptable carrier and, in an amount effective to antagonize the 5-HT$_6$ receptor, a compound of according to claim 10.

28. A pharmaceutical composition, comprising a pharmaceutically acceptable carrier and, in an amount effective to antagonize the 5-HT$_6$ receptor, a compound of according to claim 22.

29. A method for treating a patient having a medical condition for which a 5-HT$_6$ receptor antagonist is indicated, comprising administering to the patient a 5-HT$_6$ receptor antagonizing-effective amount of a compound according to claim 1.

30. The method of claim 29, wherein the medical condition is schizophrenia.

* * * * *